(12) United States Patent
Tanaka et al.

(10) Patent No.: US 6,538,152 B1
(45) Date of Patent: Mar. 25, 2003

(54) PHENOXYACETIC ACID DERIVATIVES AND MEDICINAL COMPOSITIONS CONTAINING THE SAME

(75) Inventors: Nobuyuki Tanaka, Toyoshina-machi (JP); Tetsuro Tamai, Misato-mura (JP); Harunobu Mukaiyama, Hotaka-machi (JP); Akihito Hirabayashi, Hotaka-machi (JP); Hideyuki Muranaka, Toyoshina-machi (JP); Masaaki Sato, Azusagawa-mura (JP); Masuo Akahane, Matsumoto (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 09/720,976

(22) PCT Filed: Jul. 5, 1999

(86) PCT No.: PCT/JP99/03611

§ 371 (c)(1),
(2), (4) Date: Jan. 3, 2001

(87) PCT Pub. No.: WO00/02846

PCT Pub. Date: Jan. 20, 2000

(30) Foreign Application Priority Data

Jul. 8, 1998 (JP) .......................................... 10-228501

(51) Int. Cl.$^7$ ............................................. C07C 229/00
(52) U.S. Cl. ...................... 560/42; 562/451; 564/165; 514/532; 514/539; 514/540; 514/567; 514/568; 514/617
(58) Field of Search .................. 514/532, 539, 514/546, 568, 567, 617, 619; 560/42; 562/451; 564/165

(56) References Cited

U.S. PATENT DOCUMENTS

| | | | |
|---|---|---|---|
| 3,410,944 A | | 11/1968 | Hendrick et al. |
| 4,338,333 A | * | 7/1982 | Ainsworth et al. ......... 424/309 |
| 5,776,983 A | * | 7/1998 | Washburn ................... 514/605 |

FOREIGN PATENT DOCUMENTS

| | | | |
|---|---|---|---|
| EP | 0 023 385 A | | 2/1981 |
| EP | 170121 | * | 2/1986 ........... C07C/93/14 |
| WO | WO 98/13333 A1 | | 4/1998 |
| WO | Wo 99/05090 A1 | | 2/1999 |

OTHER PUBLICATIONS

Sher P M et al. "Carboxyl–promoted enhancement of selectivity for the beta3 adrenergic receptor. Negative charge of the sulfonic acid BMS–187413 introduces beta3 binding selectivity" Bioorganic & Medicinal Chemistry Letters, Oxford, GB, vol. 7, No. 12, Jun. 17, 1997, pp. 1583–1588.

* cited by examiner

Primary Examiner—Paul J. Killos
(74) Attorney, Agent, or Firm—Sughrue Mion, PLLC

(57) ABSTRACT

The present invention provides novel phenoxyacetic acid derivatives represented by the general formula:

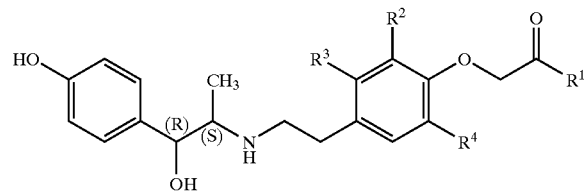

wherein $R^1$ represents a hydroxy group, a lower alkoxy group, an aralkoxy group, an amino group, or a mono or di(lower alkyl)amino group; one of $R^2$ and $R^3$ is a hydrogen atom, a halogen atom, a lower alkyl group or a lower alkoxy group, while the other is a hydrogen atom; $R^4$ represents a halogen atom, a lower alkyl group, a halo(lower alkyl) group, a hydroxy group, a lower alkoxy group, an aralkoxy group, a cyano group, a nitro group, an amino group, a mono or di(lower alkyl)amino group, a carbamoyl group, a mono or di(lower alkyl)carbamoyl group or a group represented by the general formula:

—NHCOR$^5$ (wherein $R^5$ represents a hydrogen atom or a lower alkyl group); the carbon atom marked with (R) represents a carbon atom in R configuration; and the carbon atom marked with (S) represents a carbon atom in S configuration, and pharmaceutically acceptable salts thereof, which have excellent β$_3$-adrenoceptor stimulating effects and are useful as agents for the prevention or treatment of obesity, hyperglycemia, the diseases caused by intestinal hypermotility, pollakiuria, urinary incontinence, depression, or the diseases caused by biliary calculi or hypermotility of biliary tract.

12 Claims, No Drawings

PHENOXYACETIC ACID DERIVATIVES AND MEDICINAL COMPOSITIONS CONTAINING THE SAME

TECHNICAL FIELD

The present invention relates to novel phenoxyacetic acid derivatives and pharmaceutically acceptable salts thereof which are useful as medicaments.

BACKGROUND ART

It is known that three subtypes of sympathetic β-adrenoceptor, which have been classified as $\beta_1$, $\beta_2$, and $\beta_3$ are present and that each receptor subtype is distributed in specified organs in living body and has specific function.

For example, $\beta_2$-adrenoceptor is mainly present in the heart and the stimulation of this receptor leads to increment of heart rate and cardiac contractility. $\beta_2$-Adrenoceptor is mainly present in smooth muscle of blood vessels, the trachea and uterus. The stimulation of this receptor leads to vasodilation, bronchodilation and inhibition of uterine contraction. $\beta_3$-Adrenoceptor is mainly present in adipocytes, the gallbladder and intestinal tract. It is known that $\beta_3$-adrenoceptor is also present in the brain, liver, stomach, prostate and so on. It is reported that the stimulation of this receptor leads to increment of lipolysis, inhibition of intestinal tract motility, increment of glucose uptake, antidepression and so on (Drugs of the Future, Vol.18, No.6, pp.529–549 (1993); Molecular Brain Research, Vol.29, pp.369–375 (1995); European Journal of Pharmacology, Vol.289, pp.223–228 (1995); Pharmacology, Vol.51, pp.288–297 (1995)).

In addition, it is recently reported that in human bladder $\beta_3$-adrenoceptor is predominantly present and that human bladder is relaxed by $\beta_3$-adrenoceptor stimulants (The Japanese Journal of Urology, Vol.88, No.2, p.183 (1997); Neurourology and Urodynamics, Vol.16, No.5, pp.363–365 (1997)).

Up to this time, many $\beta_1$-adrenoceptor stimulants and $\beta_2$-adrenoceptor stimulants have been developed and are used for medicinal purposes as cardiotonics, bronchodilators, preventive agents for threatened abortion or premature labor and so on.

On the other hand, it has been found that $\beta_3$-adrenoceptor stimulants are useful as agents for the prevention or treatment of obesity, hyperglycemia, the diseases caused by intestinal hyper-motility, pollakiuria, urinary incontinence, depression, the diseases caused by biliary calculi or hypermotility of biliary tract, or so on. Therefore, studies have been being actively made to develop excellent $\beta_3$-adrenoceptor stimulants, but any $\beta_3$-adrenoceptor stimulant has not been sold yet (Drugs of the Future, Vol.18, No.6, pp.529–549(1993); European Journal of Pharmacology, Vol.219, pp.193–201(1992) etc.).

Consequently, it has been greatly desired to develop novel $\beta_3$-adrenoceptor stimulants having excellent $\beta_3$-adrenoceptor stimulating effects.

More preferably, it has been desired to develop highly selective and novel $\beta_3$-adrenoceptor stimulants having potent $\beta_3$-adrenoceptor stimulating effects in comparison with $\beta_1$ and/or $\beta_2$-adrenoceptor stimulating effects and resulting in reduced side effects caused by $\beta_1$ and/or $\beta_2$-adrenoceptor stimulating effects such as palpitation and tremor.

DISCLOSURE OF THE INVENTION

The present invention relates to a phenoxyacetic acid derivative represented by the general formula:

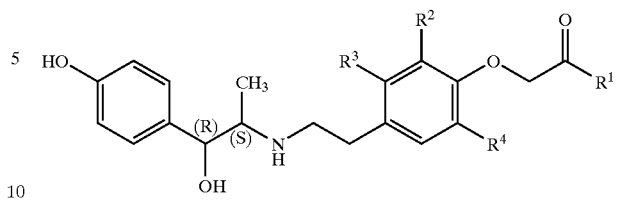

wherein $R^1$ represents a hydroxy group, a lower alkoxy group, an aralkoxy group, an amino group, or a mono or di(lower alkyl)amino group; one of $R^2$ and $R^3$ is a hydrogen atom, a halogen atom, a lower alkyl group or a lower alkoxy group, while the other is a hydrogen atom; $R^4$ represents a halogen atom, a lower alkyl group, a halo (lower alkyl) group, a hydroxy group, a lower alkoxy group, an aralkoxy group, a cyano group, a nitro group, an amino group, a mono or di(lower alkyl)amino group, a carbamoyl group, a mono or di (lower alkyl)carbamoyl group or a group represented by the general formula:

—NHCOR⁵

(wherein $R^5$ represents a hydrogen atom or a lower alkyl group); the carbon atom marked with (R) represents a carbon atom in R configuration; and the carbon atom marked with (S) represents a carbon atom in S configuration, or a pharmaceutically acceptable salt thereof.

The present invention relates to a pharmaceutical composition comprising as the active ingredient a phenoxyacetic acid derivative represented by the above general formula (I) or a pharmaceutically acceptable salt thereof.

The present invention relates to an agent for the prevention or treatment of obesity, hyperglycemia, the diseases caused by intestinal hypermotility, pollakiuria, urinary incontinence, depression, or the diseases caused by biliary calculi or hypermotility of biliary tract, which comprises as the active ingredient a phenoxyacetic acid derivative represented by the above general formula (I) or a pharmaceutically acceptable salt thereof.

The present invention relates to a method for the prevention or treatment of obesity, hyperglycemia, the diseases caused by intestinal hypermotility, pollakiuria, urinary incontinence, depression, or the diseases caused by biliary calculi or hypermotility of biliary tract, which comprises administering a therapeutically effective amount of a phenoxyacetic acid derivative represented by the above general formula (I) or a pharmaceutically acceptable salt thereof.

The present invention relates to a use of a phenoxyacetic acid derivative represented by the above general formula (I) or a pharmaceutically acceptable salt thereof for the manufacture of a pharmaceutical composition for the prevention or treatment of obesity, hyperglycemia, the diseases caused by intestinal hypermotility, pollakiuria, urinary incontinence, depression, or the diseases caused by biliary calculi or hypermotility of biliary tract.

The present invention relates to a use of a phenoxyacetic acid derivative represented by the above general formula (I) or a pharmaceutically acceptable salt thereof as an agent for the prevention or treatment of obesity, hyperglycemia, the diseases caused by intestinal hypermotility, pollakiuria, urinary incontinence, depression, or the diseases caused by biliary calculi or hypermotility of biliary tract.

The present invention relates to a process for the manufacture of a pharmaceutical composition for the prevention or treatment of obesity, hyperglycemia, the diseases caused by intestinal hyper-motility, pollakiuria, urinary incontinence, depression, or the diseases caused by biliary calculi or hypermotility of biliary tract, characterized in the use, as an essential constituent of said pharmaceutical composition, of a phenoxyacetic acid derivative represented by the above general formula (I) or a pharmaceutically acceptable salt thereof.

BEST MODE FOR CARRYING OUT THE INVENTION

The present inventors have studied earnestly to solve the above objects. As a result, it was found that phenoxyacetic acid derivatives represented by the above general formula (I) and pharmaceutically acceptable salts thereof have excellent $\beta_3$-adrenoceptor stimulating effects, thereby forming the basis of the present invention.

In the present invention, the term "halogen atom" means a fluorine atom, a chlorine atom, a bromine atom or an iodine atom; the term "lower alkyl group" means a straight or branched alkyl group having 1 to 6 carbon atoms such as a methyl group, an ethyl group, apropyl group, an isopropyl group, a butyl group, an isobutyl group, a sec-butyl group, a tert-butyl group, a pentyl group, an isopentyl group, a hexyl group or the like; the term "lower alkoxy group" means a straight or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a hexyloxy group or the like; the term "aralkoxy group" means the above lower alkoxy group substituted by an aryl group such as a phenyl group, a naphthyl group or the like; the term "mono or di(lower alkyl)amino group" means an amino group which is mono- or di-substituted by same or different lower alkyl groups as mentioned above; the term "halo (lower alkyl) group" means the above lower alkyl group substituted by same or different 1 to 5 halogen atoms as mentioned above; and the term "mono or di(lower alkyl)carbamoyl group" means a carbamoyl group which is mono- or di-substituted by same or different lower alkyl group as mentioned above.

The compounds represented by the above general formula (I) of the present invention can be prepared according to the following procedures. For example, the compounds of the present invention can be prepared by subjecting an amine compound represented by the formula:

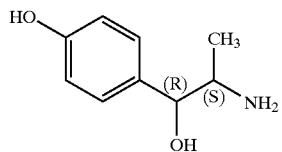

(II)

wherein the carbon atom marked with (R) and the carbon atom marked with (S) have the same meanings as defined above, to alkylation using an alkylating agent represented by the general formula:

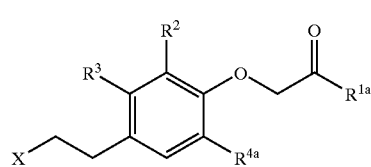

(III)

wherein $R^{1a}$ represents a lower alkoxy group, an aralkoxy group, an amino group, or a mono or di(lower alkyl)amino group; $R^{4a}$ represents a halogen atom, a lower alkyl group, a halo(lower alkyl) group, a lower alkoxy group, an aralkoxy group, a cyano group, a nitro group, a protected amino group, a protected mono(lower alkyl)amino group, a di(lower alkyl)amino group, a carbamoyl group, a mono or di(lower alkyl)carbamoyl group or a group represented by the general formula:

—NHCOR$^5$ (wherein $R^5$ has the same meaning as defined above); X represents a leaving group; and $R^2$ and $R^3$ have the same meanings as defined above, in the presence or absence of a base such as N,N-diisopropylethylamine in an inert solvent such as N,N-dimethylformamide, removing the protective group in the usual way as occasion demands, and hydrolyzing the ester group or amide group in the usual way as occasion demands.

Of the compounds represented by the above general formula (I), the compounds wherein $R^1$ is an amino group, or a mono or di(lower alkyl)amino group can be prepared by subjecting an amine compound represented by the above formula (II) to alkylation using an alkylating agent represented by the general formula:

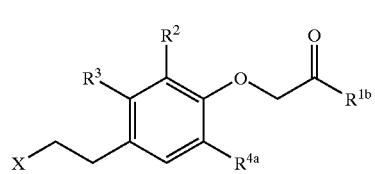

(IIIa)

wherein $R^{1b}$ represents a lower alkoxy group; and $R^2$, $R^3$, $R^{4a}$ and X have the same meanings as defined above, in the presence or absence of a base such as N,N-diisopropylethylamine in an inert solvent such as N,N-dimethylformamide, converting the aralkoxy group into a hydroxy group or removing the protective group in the usual way as occasion demands, and subjecting the resulting compound to amidation using the corresponding amine compound in the usual way.

The amine compound represented by the above formula (II) which is used as a starting material in the above production processes can be prepared by optical resolution of a commercially available enantiomeric mixture in the usual way or a method described in a literature (e.g., J. Med. Chem., Vol. 20, No. 7, pp.978–981(1977)).

Processes for the preparation of the compounds represented by the above general formula (III) or (IIIa) which are used as starting materials in the above production processes are exemplified as follows.

Of the compounds represented by the above general formula (III) or (IIIa), compounds represented by the general formula (IIIb) in the following scheme can be prepared by the following Method 1.

Method 1

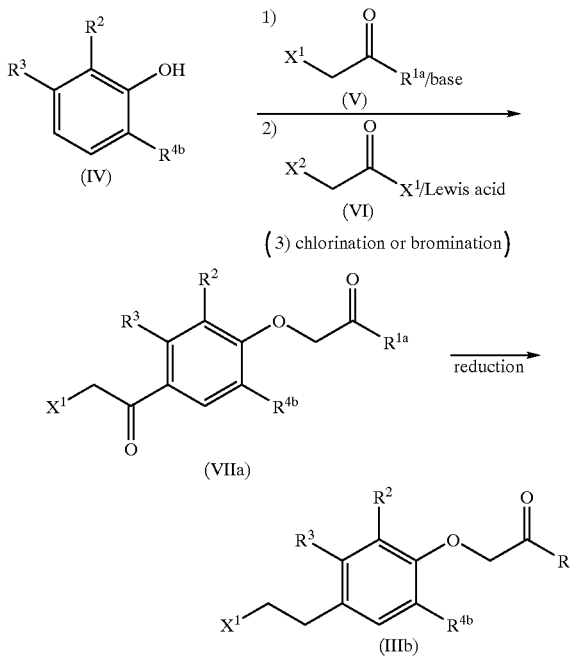

(wherein $R^{4b}$ represents a halogen atom, a lower alkyl group, a halo(lower alkyl) group, a lower alkoxy group or an aralkoxy group; $X^1$ represents a chlorine atom or a bromine atom; $X^2$ represents a hydrogen atom, a chlorine atom or a bromine atom; $R^{1a}$, $R^2$ and $R^3$ have the same meanings as defined above)

A phenol derivative represented by the general formula (IV) is allowed to react with an alkylating agent represented by the general formula (V) in the presence of a base such as potassium carbonate or N,N-diisopropylethylamine in an inert solvent such as N,N-dimethylformamide to alkylate the phenolic hydroxy group. The benzene ring of the resulting compound is acylated by Friedel-Crafts reaction using an acid halide compound represented by the general formula (VI), and the acetyl group of the resulting compound is chlorinated or brominated in the usual way as occasion demands to prepare a compound represented by the general formula (VIIa). The compound represented by the general formula (VIIa) is reduced using a reducing agent such as triethylsilane to prepare a compound represented by the general formula (IIIb).

Of the compounds represented by the above general formula (III) or (IIIa), compounds represented by the general formula (IIIc) in the following scheme can be prepared by the following Method 2.

Method 2

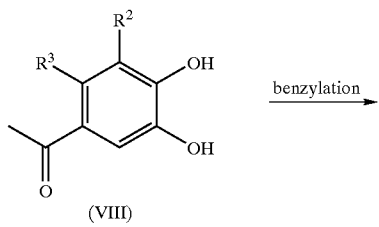

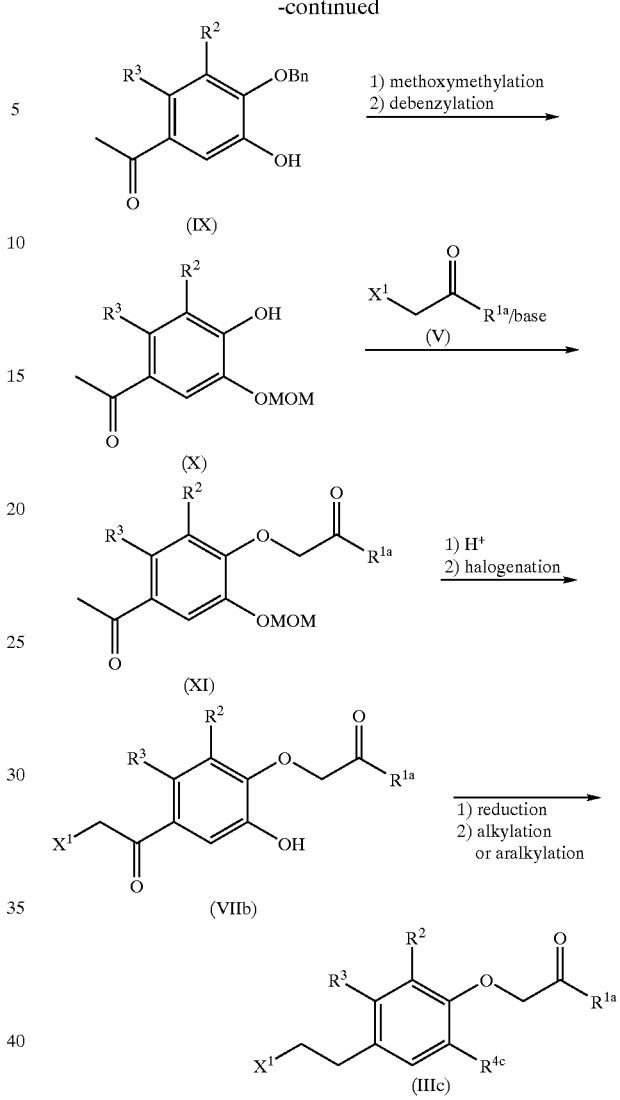

(wherein $R^{4c}$ represents a lower alkoxy group or an aralkoxy group; Bn represents a benzyl group; MOM represents a methoxymethyl group; and $R^{1a}$, $R^2$, $R^3$ and $X^1$ have the same meanings as defined above)

A phenol derivative represented by the general formula (VIII) is allowed to react with benzyl bromide in the presence of lithium carbonate in N,N-dimethylformamide to prepare a compound represented by the general formula (IX). The other phenolic hydroxy group of the resulting compound represented by the general formula (IX) is protected using chloromethyl methyl ether, and the benzyl group is removed in the usual way to prepare a compound represented by the general formula (X).

The compound represented by the general formula (X) is allowed to react with an alkylating agent represented by the general formula (V) in the presence of a base such as potassium carbonate or N,N-diisopropylethylamine in an inert solvent such as N,N-dimethylformamide to prepare a compound represented by the general formula (XI). A compound represented by the general formula (VIIb) is prepared by treating the compound represented by the general formula (XI) under acidic condition to remove the methoxymethyl group and subjecting the acetyl group of the resulting compound to halogenation in the usual way, or by subjecting the compound represented by the general formula (XI) to bromination using pyrrolidone hydrotribromide or the like under acidic condition to remove the methoxymethyl group and brominate the acetyl group at the same time.

After the compound represented by the general formula (VIIb) is reduced using a reducing agent such as triethylsilane, the phenolic hydroxy group of the resulting compound is alkylated or aralkylated in the usual way to prepare a compound represented by a general formula (IIIc).

Of the compounds represented by the above general formula (III) or (IIIa), compounds represented by the general formula (IIId) in the following scheme can be prepared by the following Method 3.

Method 3

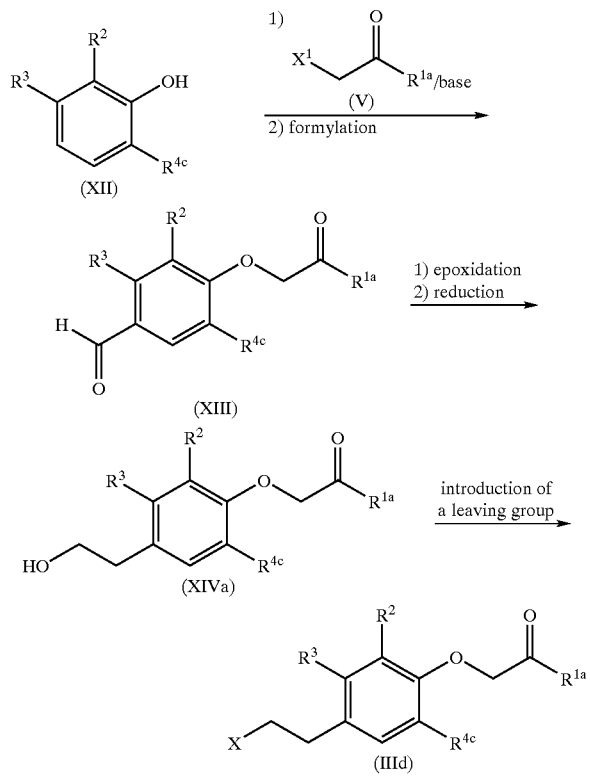

(wherein $R^{1a}$, $R^2$, $R^3$, $R^{4c}$, X and $X^1$ have the same meanings as defined above)

A phenol derivative represented by the general formula (XII) is alkylated with an alkylating agent represented by the general formula (V) in the presence of a base such as potassium carbonate or N,N-diisopropylethylamine in an inert solvent such as N,N-dimethylformamide. The benzene ring of the resulting compound is formylated with trifluoroacetic acid and hexa-methylenetetramine to prepare a compound represented by the general formula (XIII). After the formyl group of the compound (XIII) is converted into an epoxy group in the usual way, the epoxy group is reductively cloven in the usual way to prepare a compound represented by the general formula (XIVa). The alcoholic hydroxy group of the compound represented by the general formula (XIVa) is converted into a leaving group in the usual way to prepare a compound represented by the general formula (IIId).

Of the compounds represented by the above general formula (III) or (IIIa), compounds represented by the general formula (IIIe) in the following scheme can be prepared by the following Method 4.

Method 4

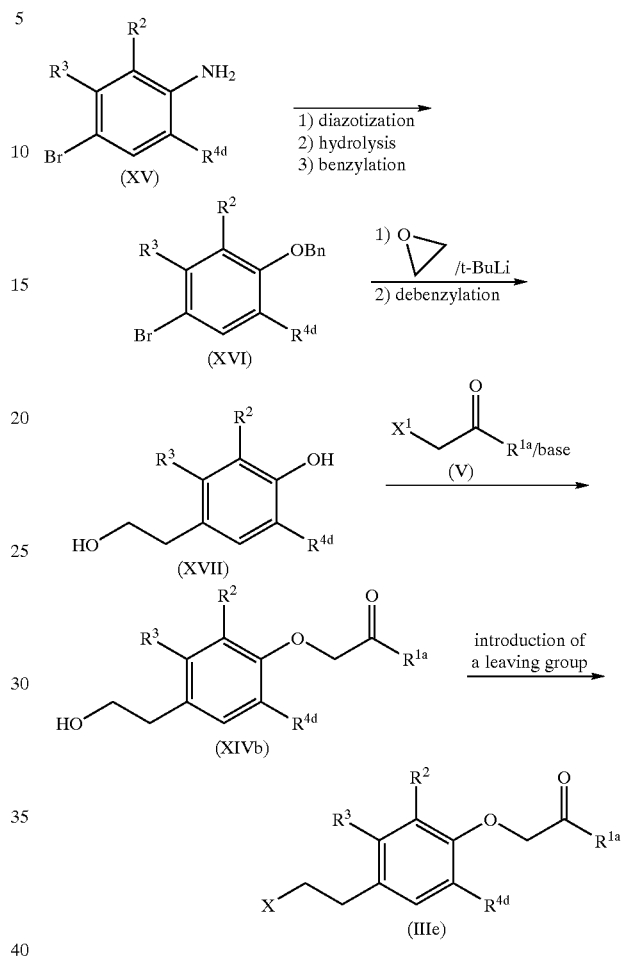

(wherein $R^{4d}$ represents a halogen atom, a lower alkyl group or a halo(lower alkyl) group; and $R^{1a}$, $R^2$, $R^3$ $X^1$ and Bn have the same meanings as defined above)

An aniline derivative represented by the general formula (XV) is diazotized in the usual way, and the resulting compound is hydrolyzed to convert into a phenol derivative. The phenol compound is benzylated with benzyl halide such as benzyl bromide to prepare a compound represented by the general formula (XVI).

A phenol derivative represented by the general formula (XVII) is prepared by allowing the compound represented by the general formula (XVI) to react with ethylene oxide in the presence of a strong base such as tert-butyl lithium in an inert solvent such as diethyl ether or tetrahydrofuran, and subjecting the resulting compound to debenzylation in the usual way. The resulting phenol derivative represented by the general formula (XVII) is alkylated with an alkylating agent represented by the general formula (V) in the presence of a base such as potassium carbonate or N,N-diisopropylethylamine in an inert solvent such as N,N-dimethylformamide to prepare a compound represented by the general formula (XIVb). The alcoholic hydroxy group of the compound represented by the general formula (XIVb) is converted into a leaving group in the usual way to prepare a compound represented by the general formula (IIIe).

Of the compounds represented by the above general formula (III) or (IIIa), compounds represented by the general formula (IIIf) in the following scheme can be prepared by the following Method 5.

Method 5

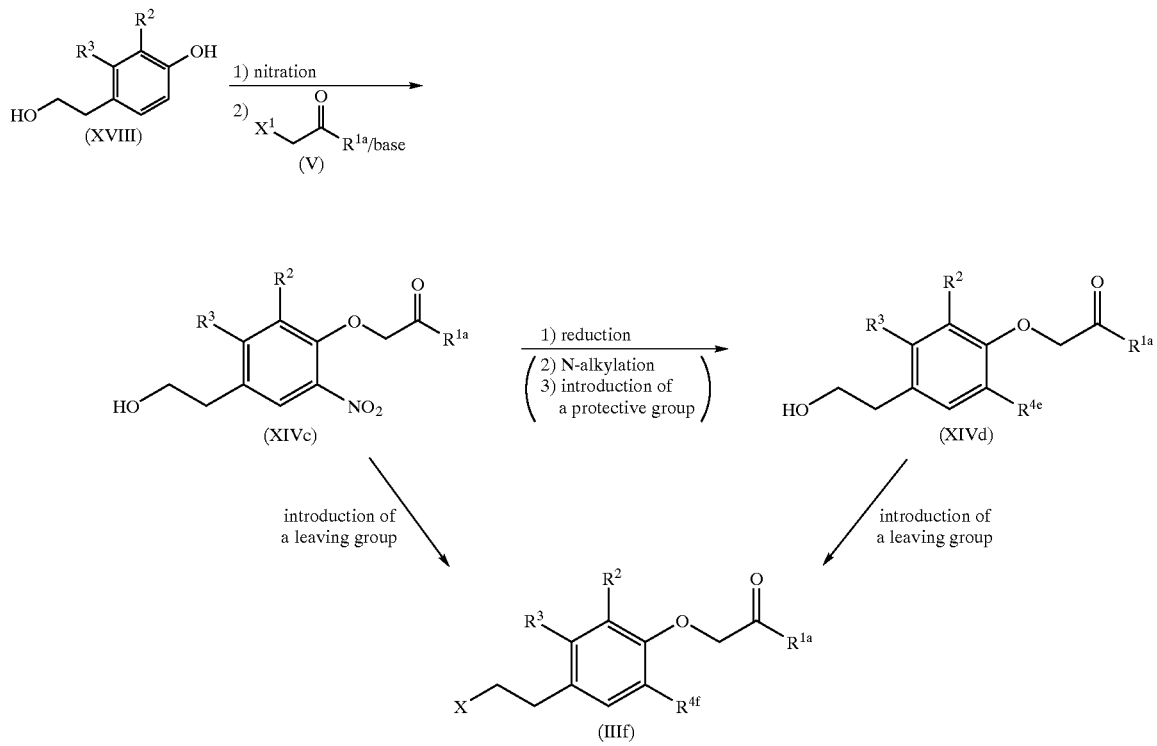

(wherein $R^{4e}$ represents a protected amino group, a protected mono(lower alkyl)amino group or a di(lower alkyl) amino group; $R^{4f}$ represents a nitro group, a protected amino group, a protected mono(lower alkyl)amino group or a di(lower alkyl)amino group; and $R^{1a}$, $R^2$, $R^3$, X and $X^1$ have the same meanings as defined above)

A compound represented by the general formula (XIVc) is prepared by subjecting a phenol derivative represented by the general formula (XVIII) to nitration in the usual way, and subjecting the phenolic hydroxy group of the resulting compound to alkylation using an alkylating agent represented by the general formula (V) in the presence of a base such as potassium carbonate or N,N-diisopropylethylamine in an inert solvent such as N,N-dimethylformamide. The nitro group of the compound represented by the general formula (XIVc) is reduced in the usual way to derive into an amine compound, and the amino group of the resulting compound is alkylated or protected as occasion demands to prepare a compound represented by the general formula (XIVd).

Of the compounds represented by the above general formula (XIVd), compounds wherein $R^{4e}$ is a dimethylamino group can be also prepared by catalytic hydrogenation of the compound represented by the general formula (XIVc) in the presence of formaldehyde in the usual way.

The alcoholic hydroxy group of the obtained compound represented by the general formulae (XIVc) or (XIVd) is converted into a leaving group in the usual way to prepare a compound represented by the general formula (IIIf).

Of the compounds represented by the above general formula (III) or (IIIa), compounds represented by the general formula (IIIg) in the following scheme can be prepared by the following Method 6.

Method 6

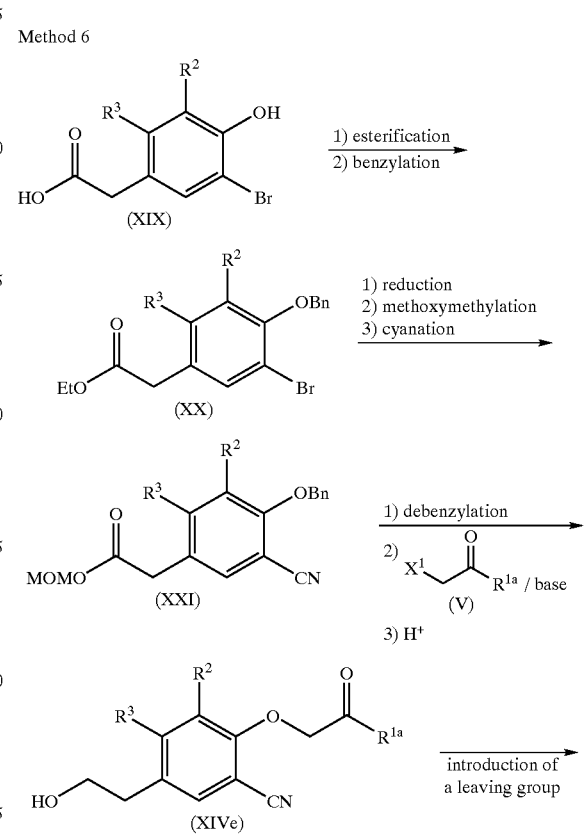

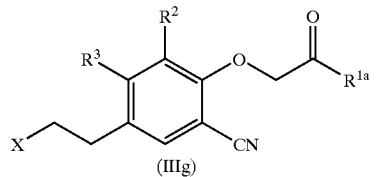

(IIIg)

(wherein Et represents an ethyl group; and $R^{1a}$, $R^2$, $R^3$, X, $X^1$, Bn and MOM have the same meanings as defined above)

A phenylacetic acid derivative represented by the general formula (XIX) is esterified and benzylated in the usual way to prepare a compound represented by the general formula (XX). A compound represented by the general formula (XXI) is prepared by reducing the compound represented by the general formula (XX) using a reducing agent such as lithium aluminum hydride in an inert solvent such as diethyl ether or tetrahydrofuran, protecting the alcoholic hydroxy group of the resulting compound with chloromethyl methyl ether in the usual way, and subjecting the benzene ring of the resulting compound to cyanation using copper cyanide or the like.

The benzyl group of the compound represented by the general formula (XXI) is removed in the usual way. The resulting compound is alkylated with an alkylating agent represented by the general formula (V) in the presence of a base such as potassium carbonate or N,N-diisopropylethylamine in an inert solvent such as N,N-dimethylformamide, and the methoxymethyl group is removed by treating the resulting compound under acidic condition to prepare a compound represented by the general formula (XIVe). The alcoholic hydroxy group of the resulting compound represented by the general formula (XIVe) is converted into a leaving group in the usual way to prepare a compound represented by the general formula (IIIg).

Of the compounds represented by the above general formula (III) or (IIIa), compounds represented by the general formula (IIIh) in the following scheme can be prepared by the following Method 7.

Method 7

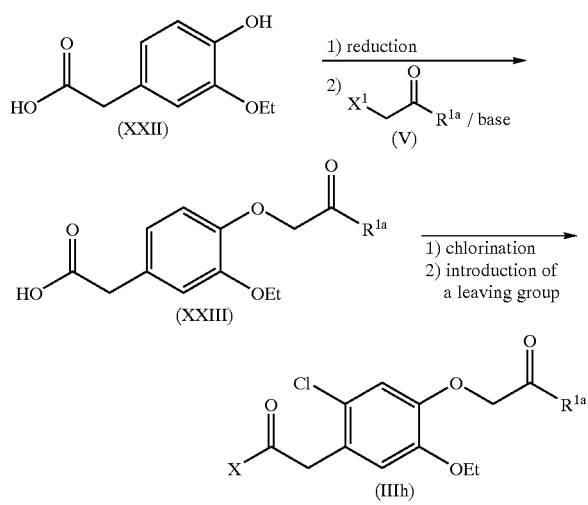

(wherein $R^{1a}$, X, $X^1$ and Et have the same meanings as defined above)

An alcohol compound represented by the general formula (XXIII) is prepared by reducing the phenylacetic acid derivative represented by the formula (XXII) with a reducing agent such as borane-dimethylsulfide complex in an inert solvent such as diethyl ether or tetrahydrofuran, and subjecting the phenolic hydroxy group of the resulting compound to alkylation using an alkylating agent represented by the general formula (V) in the presence of a base such as potassium carbonate or N,N-diisopropylethylamine in an inert solvent such as N,N-dimethylformamide. After the alcohol compound represented by the general formula (XXIII) is allowed to react with a chlorinating agent such as tert-butylhypochlorite in an inert solvent such as dichloromethane or chloroform, the alcoholic hydroxy group is converted into a leaving group in the usual way to prepare a compound represented by the general formula (IIIh).

Of the compounds represented by the above general formula (III) or (IIIa), compounds represented by the general formula (IIIi) in the following scheme can be prepared by the following Method 8.

Method 8

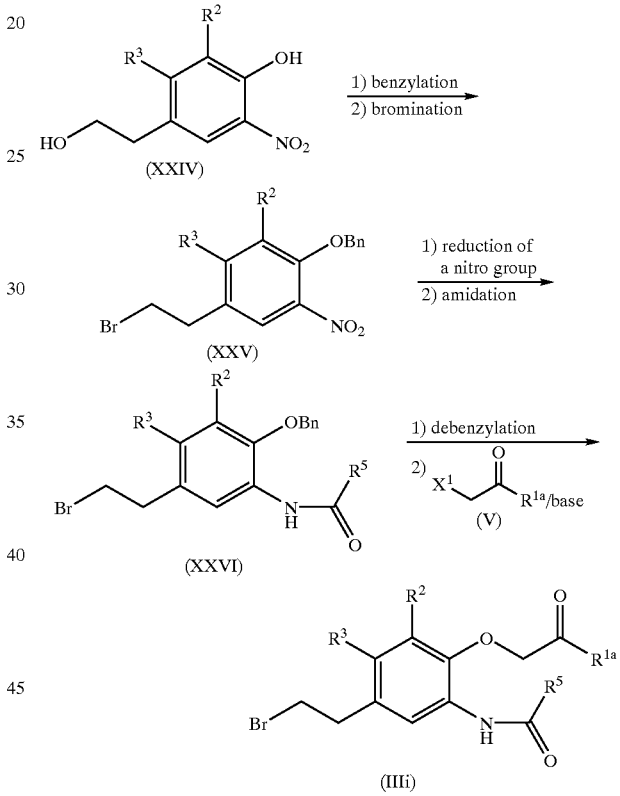

(wherein $R^{1a}$, $R^2$, $R^3$, $R^5$, $X^1$ and Bn have the same meanings as defined above)

The phenolic hydroxy group of a phenol derivative represented by the general formula (XXIV) is benzylated in the usual way, and the alcoholic hydroxy group of the resulting compound is converted into a bromine atom by bromination reaction using triphenylphosphine and carbon tetrabromide in an inert solvent such as diethyl ether or tetrahydrofuran to prepare a compound represented by the general formula (XXV).

After the nitro group of the compound represented by the general formula (XXV) is reduced in the usual way, the amino group of the resulting compound is converted into an amide group using a reactive functional derivative such as an acid halide or an active ester to prepare a compound represented by the general formula (XXVI). The compound represented by the general formula (IIIi) is prepared by subjecting the compound represented by the general formula (XXVI) to debenzylation in the usual way and subjecting the resulting compound to alkylation using an alkylating agent represented by the general formula (V) in the presence of a base such as potassium carbonate or N,N-diisopropylethylamine in an inert solvent such as N,N-dimethylformamide.

Of the compounds represented by the above general formula (III) or (IIIa), compounds represented by the general formula (IIIj) in the following scheme can be prepared by the following Method 9.

Method 9

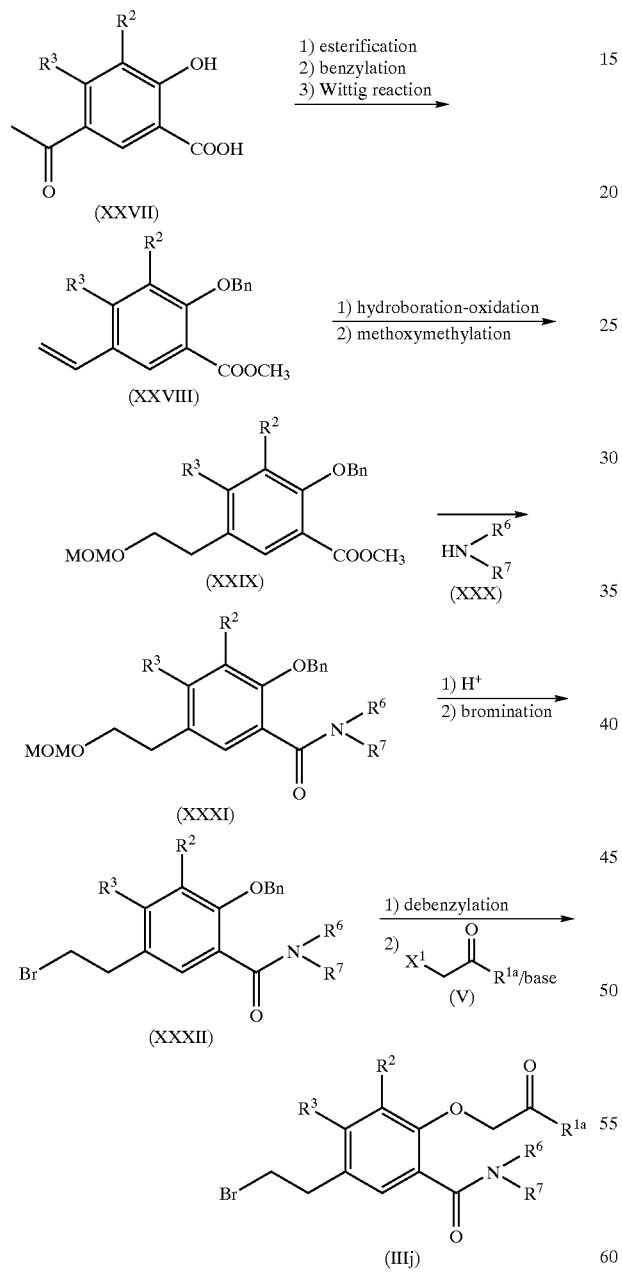

(wherein $R^6$ and $R^7$ are the same or different and each represents a hydrogen atom or a lower alkyl group; and $R^{1a}$, $R^2$, $R^3$, $X^1$, Bn and MOM have the same meanings as defined above)

A styrene derivative represented by the general formula (XXVIII) is prepared by subjecting a benzoic acid derivative represented by the general formula (XXVII) to esterification and benzylation in the usual way and subjecting the resulting compound to Wittig reaction using methyltriphenylphosphonium bromide or the like.

A compound represented by the general formula (XXIX) is prepared by converting the styrene derivative represented by the general formula (XXVIII) by hydroboration-oxidation method using a borane agent such as 9-borabicyclo[3.3.1]nonane and a peroxide compound such as hydroperoxide in an inert solvent such as diethyl ether or tetrahydrofuran into an alcohol derivative and protecting the alcoholic hydroxy group of the resulting alcohol derivative using chloromethyl methyl ether.

A compound represented by the general formula (XXXI) is prepared by allowing the compound represented by the general formula (XXIX) to react with an amine compound represented by the general formula (XXX), or by hydrolyzing the compound represented by the general formula (XXIX), converting the resulting benzoic acid derivative into a reactive functional derivative such as an acid halide or an active ester in the usual way, and allowing the resulting compound to react with the amine compound represented by the general formula (XXX) After the compound represented by the general formula (XXXI) is treated under acidic condition to remove the methoxymethyl group, the resulting alcoholic hydroxy group is converted into a bromine atom in the usual way to prepare a compound represented by the general formula (XXXII).

After debenzylation of the compound represented by the general formula (XXXII) in the usual way, the resulting compound is alkylated with an alkylating agent represented by the general formula (V) in the presence of a base such as potassium carbonate or N,N-diisopropylethylamine in an inert solvent such as N,N-dimethylformamide to prepare a compound represented by the general formula (IIIj).

Of the compounds represented by the above general formula (III) or (IIIa), compounds represented by the general formula (IIIk) in the following scheme can be prepared by the following Method 10.

Method 10

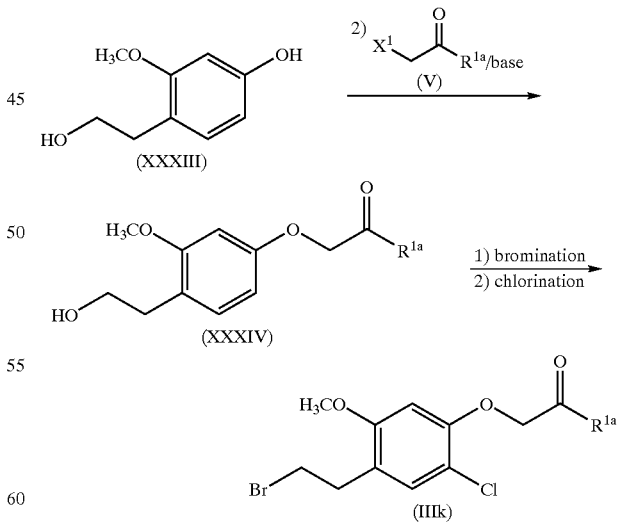

(wherein $R^{1a}$ and $X^1$ have the same meanings as defined above)

The phenol derivative represented by the formula (XXXIII) is alkylated with an alkylating agent represented by the general formula (V) in the presence of abase such as potassium carbonate or N,N-diisopropylethylamine in an inert solvent such as N,N-dimethylformamide to prepare a compound represented by the general formula (XXXIV) The compound represented by the general formula (IIIk) is prepared by converting the alcoholic hydroxy group of the compound represented by the general formula (XXXIV) into a bromine atom by bromination reaction using triphenylphosphine and carbon tetrabromide in an inert solvent such as diethyl ether or tetrahydrofuran, and allowing the resulting compound to react with a chlorinating agent such as tert-butylhypochlorite in an inert solvent such as dichloromethane or chloroform.

Of the compounds represented by the above general formula (III) or (IIIa), compounds represented by the general formula (IIIm) in the following scheme can be prepared by the following Method 11.

Method 11

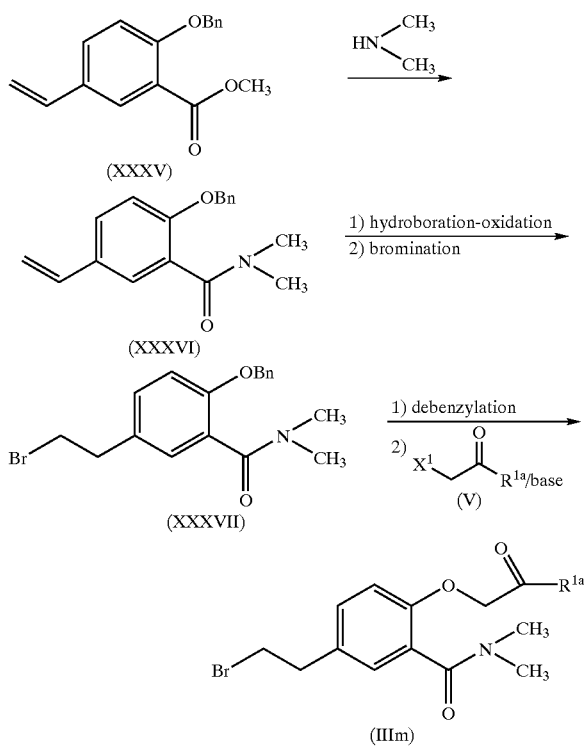

(wherein $R^{1a}$, $X^1$ and Bn have the same meanings as defined above)

The compound represented by the formula (XXXVI) is prepared by allowing the benzoate derivative represented by the formula (XXXV) to react with dimethylamine, or by hydrolyzing the benzoate derivative represented by the formula (XXXV) to convert it into a benzoic acid derivative in the usual way, deriving the benzoic acid derivative into a reactive functional derivative such as an acid halide or an active ester, and allowing the resulting compound to react with dimethylamine.

The compound represented by the formula (XXXVI) is converted into an alcohol derivative by hydroboration-oxidation method using a borane agent such as 9-borabicyclo-[3.3.1]nonane and a peroxide compound such as hydroperoxide in an inert solvent such as diethyl ether or tetrahydrofuran. The alcoholic hydroxy group of the resulting derivative is converted into a bromine atom by bromination reaction using triphenylphosphine and carbon tetrabromide in an inert solvent such as diethyl ether or tetrahydrofuran to prepare the compound represented by the general formula (XXXVII). After debenzylation of the compound represented by the general formula (XXXVII) in the usual way, the phenolic hydroxy group of the resulting compound is alkylated using an alkylating agent represented by the general formula (V) in the presence of a base such as potassium carbonate or N,N-diisopropylethylamine in an inert solvent such as N,N-dimethylformamide to prepare a compound represented by the general formula (IIIm).

In the above production processes, the terms "protected amino group" and "protected mono(lower alkyl)amino group" mean an amino group and a mono(lower alkyl)amino group which are protected by a protective group generally used as an amino protective group such as a tert-butoxycarbonyl group, a benzyloxycarbonyl group and the like; and the term "leaving group" means a leaving group generally used for N-alkylation such as a p-toluenesulfonyloxy group, a methanesulfonyloxy group, a chlorine atom, a bromine atom, an iodine atom and the like.

The compounds represented by the above general formulae (IV), (V), (VI), (VIII), (XII), (XV), (XVIII), (XIX), (XXII), (XXIV), (XXVII), (XXX) and (XXXIII) which are used as starting materials in the above production processes are commercially available or can be readily prepared by a method described in a literature (International Application Publication No. WO 94/22834; ibid. No. WO 98/07710; J. Chem. Soc. Perkin Trans. I, 1994, pp. 2169–2176; S. Afr. J. Chem., Vol.34, pp. 132–133(1981) etc.).

The phenoxyacetic acid derivatives represented by the above general formula (I) of the present invention can be converted into their pharmaceutically acceptable salts in the usual way. Examples of such salts include acid addition salts formed with mineral acids such as hydrochloric acid, hydrobromic acid, hydroiodic acid, sulfuric acid, nitric acid and phosphoric acid; acid addition salts formed with organic acids such as formic acid, acetic acid, methanesulfonic acid, benzenesulfonic acid, p-toluenesulfonic acid, propionic acid, citric acid, succinic acid, tartaric acid, fumalic acid, butyric acid, oxalic acid, malonic acid, maleic acid, lactic acid, malic acid, carbonic acid, glutamic acid and aspartic acid; inorganic base salts such as a sodium salt, a potassium salt and a calcium salt; and salts formed with organic bases such as triethylamine, piperidine, morpholine, pyridine and lysine.

The compounds of the present invention include their solvates with pharmaceutically acceptable solvents such as water and ethanol.

The compounds of the present invention obtained by the above production process can be isolated and purified by conventional separation means such as fractional recrystallization, purification using chromatography and solvent extraction.

$\beta_3$-Adrenoceptor stimulating effects of the compounds represented by the above general formula (I) of the present invention were studied by the following procedure.

Namely, urinary bladders of ferrets were isolated and preparations were made. The experiment was conducted according to the Magnus method. The ureteral tension without addition of a test compound is expressed as 100%, and the tension of maximal relaxation after addition of $10^{-5}$M forskolin was expressed as 0%. The test compound was added cumulatively. The $\beta_3$-adrenoceptor stimulating effects were evaluated as the concentration of the test compound required to produce 50% decrease of the tension (i.e., $EC_{50}$ value) (The Japanese Journal of Urology, Vol.89, No.2, p.272 (1998)).

For example, $\beta_3$-adrenoceptor stimulating effect of 2-[2-chloro-4-[2-[[(1S,2R)-2-hydroxy-2-(4-hydroxyphenyl)-1- methylethyl]amino]ethyl]phenoxy]acetic acid was 4.2×10$^{-9}$M (EC$_{50}$ value).

Thus, the compounds represented by the above general formula (I) of the present invention are excellent β3-adrenoceptor stimulants having potent β$_3$-adrenoceptor stimulating effects.

The β$_1$-adrenoceptor stimulating effects and β$_2$-adrenoceptor stimulating effects of the compounds represented by the above general formula (I) of the present invention were studied by the following procedures.

Namely, the experiment was conducted using atria of rats according to the Magnus method. The increment of heart rate after addition of 10$^{-8}$M isoproterenol was expressed as 100%. A test compound was added cumulatively. The β$_1$-adrenoceptor stimulating effects were evaluated as the concentration of the test compound required to produce 50% increase of heart rate (i.e., EC$_{50}$ value).

Also, uteri of pregnant rats were isolated and preparations were made. The experiment was conducted according to the Magnus method. The sum of uterine contractions during 5 minutes before addition of a test compound was expressed as 100%. The test compound was added cumulatively. The β$_2$-adrenoceptor stimulating effects were evaluated as the concentration of the test compound required when the sum of the contractions during 5 minutes after addition of the test compound produces 50% decrease of the sum of the contractions during 5 minutes before addition of the test compound (i.e., EC$_{50}$ value).

For example, β$_1$ and β$_2$-adrenoceptor stimulating effects of 2-[2-chloro-4-[2-[[(1S,2R)-2-hydroxy-2-(4-hydroxyphenyl)-1-methylethyl]amino]ethyl]phenoxy]acetic acid were 7.0×10$^{-5}$M and 1.4×10$^{-5}$M (EC$_{50}$ value), respectively. This compound is a selective β$_3$-adrenoceptor stimulant with reduced β$_1$ and β$_2$-adrenoceptor stimulating effects in comparison with a β$_3$-adrenoceptor stimulating effect.

The phenoxyacetic acid derivatives represented by the above general formula (I) of the present invention and pharmaceutically acceptable salts thereof have excellent β$_3$-adrenoceptor stimulating effects and are very useful as agents for the prevention or treatment of obesity, hyperglycemia, the diseases caused by intestinal hypermotility such as diarrhea and irritable bowel syndrome, depression, pollakiuria, urinary incontinence, the diseases caused by biliary calculi or hypermotility of biliary tract, or the like.

Furthermore, the compounds represented by the above general formula (I) of the present invention are very safe. In acute toxicity test using rats, for example, when ethyl 2-[2-chloro-4-[2-[[(1S,2R)-2-hydroxy-2-(4-hydroxyphenyl)-1-methylethyl]amino]ethyl]phenoxy] acetate hydrochloride was administered at a dose of 2 g/kg, no death was observed.

When the phenoxyacetic acid derivatives represented by the above general formula (I) and pharmaceutically acceptable salts thereof of the present invention are employed in the practical treatment, they are administered orally or parenterally in the form of appropriate compositions such as powders, granules, fine granules, tablets, capsules, injections, solutions, ointments, suppositories, poultices and the like. These pharmaceutical compositions can be formulated in accordance with conventional methods using conventional pharmaceutical carriers, excipients and the like.

The dosage is appropriately decided depending on the age, sex, body weight and degree of symptoms of each patient to be treated, which is approximately within the range of from 1 to 1,000 mg per day per adult human in the case of oral administration and approximately within the range of from 0.01 to 100 mg per day per adult human in the case of parenteral administration, and the daily dose can be divided into one to several doses per day.

The present invention is further illustrated in more detail by way of the following Reference Examples, Examples and Test Examples. However, the present invention is not limited thereto.

Reference Example 1

Ethyl 2-[2-bromo-4-(2-bromoacetyl)phenoxy]acetate

To a solution of 2-bromophenol (3.0 ml) in acetone (52 ml) were added potassium carbonate (5.36 g) and ethyl bromoacetate (3.44 ml), and the mixture was stirred for 20 hours at room temperature. After removal of the insoluble material by filtration, the filtrate was concentrated under reduced pressure. The residue was dissolved in ethyl acetate, washed with water and brine, and dried over anhydrous magnesium sulfate. The solvent was removed under reduced pressure, and the residue was added under ice-cooling to the reaction mixture that had been stirred for 30 minutes after addition of bromoacetyl bromide (2.26 ml) to a stirred suspension of aluminum chloride (10.4 g) in 1,2-dichloroethane (86 ml). The resulting mixture was stirred for 24 hours at room temperature. The reaction mixture was poured into ice-water and extracted with dichloromethane. The extract was washed with water and dried over anhydrous magnesium sulfate. Removal of the solvent under reduced pressure gave ethyl 2-[2-bromo-4-(2-bromoacetyl)-phenoxy]acetate (4.57 g).

$^1$H-NMR(CDCl$_3$) δ ppm: 1.30 (3H, t, J=7.1 Hz),4.28 (2H, q, J=7.1 Hz), 4.36 (2H, s), 4.79 (2H, s), 6.83 (1H, d, J=8.7 Hz), 7.91 (1H, dd, J=8.7, 2.2 Hz), 8.22 (1H, d, J=2.2 Hz)

Reference Example 2

The following compounds were prepared according to a similar manner to that described in Reference Example 1 using the corresponding phenol derivative.

Ethyl 2-[4-(2-bromoacetyl)-2,5-dichlorophenoxy]acetate $^1$H-NMR(CDCl$_3$) δ ppm: 1.32 (3H, t, J=7.1 Hz), 4.31 (2H, q, J=7.1 Hz), 4.51 (2H, s), 4.76 (2H, s), 6.85 (1H, s), 7.76 (1H, s)

Ethyl 2-[4-(2-bromoacetyl)-2,5-dimethylphenoxy]acetate $^1$H-NMR(CDCl$_3$) δ ppm: 1.31 (3H, t, J=7.1 Hz), 2.30 (3H, s), 2.52 (3H, s), 4.28 (2H, q, J=7.1 Hz), 4.40 (2H, s), 4.69 (2H, s), 6.54 (1H, s), 7.56 (1H, s)

Ethyl 2-[4-(2-bromoacetyl)-2-ethylphenoxy]acetate $^1$H-NMR(CDCl$_3$) δ ppm: 1.25 (3H, t, J=7.6 Hz), 1.29 (3H, t, J=7.1 Hz), 2.75 (2H, q, J=7.6 Hz), 4.27 (2H, q, J=7.1 Hz), 4.39 (2H, s), 4.72 (2H, s), 6.74 (1H, d, J=8.5 Hz), 7.80–7.85 (2H, m)

Ethyl 2-[4-(2-bromoacetyl)-2-chloro-5-methylphenoxy]acetate $^1$H-NMR(CDCl$_3$) δ ppm: 1.37 (3H, t, J=7.1 Hz), 2.53 (3H, s), 4.29 (2H, q, J=7.1 Hz), 4.37 (2H, s), 4.77 (2H, s), 6.71 (1H, s), 7.79 (1H, s)

Ethyl 2-[4-(2-bromoacetyl)-2,5-difluorophenoxy]acetate $^1$H-NMR(CDCl$_3$) δ ppm: 1.32 (3H, t, J=7.1 Hz), 4.30 (2H, q, J=7.1 Hz), 4.46 (2H, s), 4.77 (2H, s), 6.66 (1H, dd, J=11.7, 6.4 Hz), 7.73 (1H, dd, J=11.3, 6.6 Hz)

Reference Example 3

Ethyl 2-[4-(2-bromoacetyl)-2-hydroxyphenoxy]acetate

To a solution of 3',4'-dihydroxyacetophenone (2.00 g) in N,N-dimethylformamide (40 ml) were added lithium carbonate (2.44 g) and benzyl bromide (4.0 ml), and the mixture was stirred for 14.5 hours at 50° C. To the reaction mixture was added 1N hydrochloric acid, and the resulting mixture was extracted with a mixed solution of diethyl ether and ethyl acetate (3/1). The extract was washed with water and brine, and dried over anhydrous magnesium sulfate. After the solvent was removed under reduced pressure, purification of the residue by flash column chromatography on silica gel (eluent: hexane/ethyl acetate=4/1) gave 4'-benzyloxy-3'-hydroxyacetophenone (2.00 g). To a stirred solution of the obtained 4'-benzyloxy-3'-hydroxyacetophenone (2.00 g) in dichloromethane (25 ml) was added N,N-diisopropylethylamine (2.2 ml) under ice-cooling, and the mixture was stirred for 10 minutes. Chloromethylmethyl ether (1.2 ml) was added to the mixture, and the resulting mixture was stirred for 5.5 hours at room temperature. The reaction mixture was poured into a saturated aqueous ammonium chloride solution and extracted with dichloromethane. The extract was washed with brine and dried over anhydrous magnesium sulfate. After the solvent was removed under reduced pressure, purification of the residue by flash column chromatography on silica gel (eluent: hexane/ethyl acetate=3/1) gave 4'-benzyloxy-3'-methoxymethoxyacetophenone (2.28 g).

To a solution of the obtained 4'-benzyloxy-3'-methoxymethoxyacetophenone (2.28 g) in methanol (20 ml) was added 10% palladium carbon (wet, 50% water) (687 mg), and the mixture was stirred for 1 hour at room temperature under a hydrogen atmosphere. The catalyst was filtered off, and the filtrate was concentrated under reduced pressure. The residue was dissolved in N,N-dimethylformamide (20 ml), and potassium carbonate (1.21 g) and ethyl bromoacetate (1.0 ml) were added to the solution. After the mixture was stirred for 13 hours at 40° C., the reaction mixture was poured into water and extracted with a mixed solution of diethyl ether and ethyl acetate (5/1). The extract was washed with water and brine, and dried over anhydrous magnesium sulfate. After the solvent was removed under reduced pressure, purification of the residue by flash column chromatography on silica gel (eluent: hexane/ethyl acetate=3/1) gave ethyl 2-(4-acetyl-2-methoxymethoxyphenoxy)acetate (1.52 g).

$^1$H-NMR(CDCl$_3$) δ ppm: 1.29 (3H, t, J=7.1 Hz), 2.56 (3H, s), 3.54 (3H, s), 4.27 (2H, q, J=7.1 Hz), 4.77 (2H, s), 5.30 (2H, s), 6.83 (1H, d, J=8.5 Hz), 7.61 (1H, dd, J=8.5, 2.1 Hz), 7.78 (1H, d, J=2.1 Hz)

To a solution of ethyl 2-(4-acetyl-2-methoxymethoxyphenoxy)acetate (1.51 g) in tetrahydrofuran (30 ml) was added pyrrolidone hydrotribromide (2.92 g), and the mixture was stirred for 21 hours at room temperature. The reaction mixture was poured into water and extracted with ethyl acetate. The extract was washed with brine and dried over anhydrous magnesium sulfate. After the solvent was removed under reduced pressure, purification of the residue by flash column chromatography on silica gel (eluent: hexane/diethyl ether/dichloromethane=3/2/2) and subsequent crystallization from hexane and diethyl ether (1/1) gave ethyl 2-[4-(2-bromoacetyl)-2-hydroxyphenoxy]acetate (780 mg).

$^1$H-NMR(CDCl$_3$) δ ppm: 1.31 (3H, t, J=7.1 Hz), 4.29 (2H, q, J=7.1 Hz), 4.39 (2H, s), 4.73 (2H, s), 6.79 (1H, br), 6.91 (1H, d, J=8.5 Hz), 7.54 (1H, dd, J=8.5, 2.2 Hz), 7.60 (1H, d, J=2.2 Hz)

Reference Example 4

The following compound was prepared according to a similar manner to that described in Reference Example 3 using bromoethane instead of chloromethyl methyl ether.

Ethyl 2-[4-(2-bromoacetyl)-2-ethoxyphenoxy]acetate $^1$H-NMR(CDC$_3$) δ ppm: 1.30 (3H, t, J=7.1 Hz), 1.49 (3H, t, J=7.0 Hz), 4.18 (2H, q, J=7.0 Hz), 4.28 (2H, q, J=7.1 Hz), 4.40 (2H, s), 4.77 (2H, s), 6.82 (1H, d, J=8.2 Hz), 7.50–7.60 (2H, m)

Reference Example 5

Ethyl 2-[2-bromo-4-(2-bromoethyl)phenoxy]acetate

To a solution of ethyl 2-[2-bromo-4-(2-bromoacetyl)phenoxy]acetate (2.12 g) in trifluoroacetic acid (4.29 ml) was added triethylsilane (2.67 ml), and the mixture was stirred for 1 hour at 50° C. After concentration of the reaction mixture under reduced pressure, purification of the residue by medium pressure liquid column chromatography on silica gel (eluent: hexane/ethyl acetate=5/1) gave ethyl 2-[2-bromo-4-(2-bromoethyl)phenoxy]acetate (1.84 g).

$^1$H-NMR(CDCl$_3$) δ ppm: 1.29 (3H, t, J=7.1 Hz), 3.08 (2H, t, J=7.5 Hz), 3.52 (2H, t, J=7.5 Hz), 4.27 (2H, q, J=7.1 Hz), 4.68 (2H, s), 6.77 (1H, d, J=8.4 Hz), 7.08 (1H, dd, J=8.4, 2.2 Hz), 7.42 (1H, d, J=2.2 Hz)

Reference Example 6

The following compounds were prepared according to a similar manner to that described in Reference Example 5 using the corresponding ethyl phenoxyacetate derivative.

Ethyl 2-[4-(2-bromoethyl)-2-methylphenoxy]acetate $^1$H-NMR(CDCl$_3$) δ ppm: 1.29 (3H, t, J=7.1 Hz), 2.28 (3H, s), 3.07 (2H, t, J=7.6 Hz), 3.52 (2H, t, J=7.6 Hz), 4.26 (2H, q, J=7.1 Hz), 4.62 (2H, s), 6.64 (1H, d, J=8.2 Hz), 6.96 (1H, dd, J=8.2, 1.9 Hz), 7.00 (1H, d, J=1.9 Hz)

Ethyl 2-[4-(2-bromoethyl)-2-ethylphenoxy]acetate $^1$H-NMR(CDCl$_3$) δ ppm: 1.22 (3H, t, J=7.5 Hz), 1.29 (3H, t, J=7.1 Hz), 2.69 (2H, q, J=7.5 Hz), 3.08 (2H, t, J=7.7 Hz), 3.52 (2H, t, J=7.7 Hz), 4.25 (2H, q, J=7.1 Hz), 4.61 (2H, s), 6.65 (1H, d, J=8.3 Hz), 6.96 (1H, dd, J=8.3, 2.2 Hz), 7.01 (1H, d, J=2.2 Hz)

Ethyl 2-[4-(2-bromoethyl)-2-ethoxyphenoxy]acetate $^1$H-NMR(CDCl$_3$) δ ppm: 1.29 (3H, t, J=7.1 Hz), 1.46 (3H, t, J=7.0 Hz), 3.09 (2H, t, J=7.6 Hz), 3.53 (2H, t, J=7.6 Hz), 4.10 (2H, q, J=7.0 Hz), 4.26 (2H, q, J=7.1 Hz), 4.66 (2H, s), 6.70 (1H, dd, J=8.1, 2.0 Hz), 6.75 (1H, d, J=2.0 Hz), 6.81 (1H, d, J=8.1 Hz)

Ethyl 2-[4-(2-bromoethyl)-2-hydroxyphenoxy]acetate $^1$H-NMR(CDCl$_3$) δ ppm: 1.30 (3H, t, J=7.2 Hz), 3.06 (2H, t, J=7.6 Hz), 3.52 (2H, t, J=7.6 Hz), 4.27 (2H, q, J=7.2 Hz), 4.63 (2H, s), 6.40 (1H, br), 6.66 (1H, dd, J=8.3, 2.0 Hz), 6.80–6.90 (2H, m)

Ethyl 2-[4-(2-bromoethyl)-2,5-dichlorophenoxy]acetate $^1$H-NMR(CDCl$_3$) δ ppm: 1.31 (3H, t, J=7.1 Hz), 3.19 (2H, t, J=7.5 Hz), 3.54 (2H, t, J=7.5 Hz), 4.29 (2H, q, J=7.1 Hz), 4.68 (2H, s), 6.86 (1H, s), 7.30 (1H, s)

Ethyl 2-[4-(2-bromoethyl)-2,5-dimethylphenoxy] acetate $^1$H-NMR(CDCl$_3$) δ ppm: 1.30 (3H, t, J=7.1 Hz), 2.24 (3H, s), 2.26 (3H, s), 3.00–3.10 (2H, m), 3.40–3.50 (2H, m), 4.27 (2H, q, J=7.1 Hz), 4.61 (2H, s), 6.50 (1H, s), 6.93 (1H, s)

Ethyl 2-[4-(2-bromoethyl)-2-chloro-5-methylphenoxy]acetate $^1$H-NMR(CDCl$_3$) δ ppm: 1.30 (3H, t, J=7.2 Hz), 2.27 (3H, s), 3.07 (2H, t, J=7.8 Hz), 3.47 (2H, t, J=7.8 Hz), 4.27 (2H, q, J=7.2 Hz), 4.67 (2H, s), 6.65 (1H, s), 7.17 (1H, s)

Ethyl 2-[4-(2-bromoethyl)-2,5-difluorophenoxy] acetate $^1$H-NMR(CDCl$_3$) δ ppm: 1.31 (3H, t, J=7.2 Hz), 3.11 (2H, t, J=7.3 Hz), 3.53 (2H, t, J=7.3 Hz), 4.28 (2H, q, J=7.2 Hz), 4.67 (2H, s) 6.66 (1H, dd, J=10.4, 6.9 Hz), 6.97 (1H, dd, J=11.2, 6.9 Hz)

Reference Example 7

Ethyl 2-[2-benzyloxy-4-(2-bromoethyl)phenoxy] acetate

To a solution of ethyl 2-[4-(2-bromoethyl)-2-hydroxyphenoxy]acetate (400 mg) in N,N-dimethylformamide (4 ml) were added potassium carbonate (200 mg) and benzyl bromide (0.17 ml) and the mixture was stirred for 13.5 hours at room temperature. The reaction mixture was poured into water and extracted with a mixed solution of diethyl ether and ethyl acetate (3/1). The extract was washed with water and brine, and dried over anhydrous magnesium sulfate. After the solvent was removed under reduced pressure, purification of the residue by flash column chromatography on silica gel (eluent: hexane/ethyl acetate= 17/3) gave ethyl 2-[2-benzyloxy-4-(2-bromoethyl)phenoxy] acetate (252 mg).

$^1$H-NMR(CDCl$_3$) δ ppm: 1.28 (3H, t, J=7.1 Hz), 3.05 (2H, t, J=7.6 Hz), 3.48 (2H, t, J=7.6 Hz), 4.24 (2H, q, J=7.1 Hz), 4.68 (2H, s), 5.15 (2H, s), 6.73 (1H, dd, J=8.2, 2.0 Hz), 6.79 (1H, d, J=2.0 Hz), 6.84 (1H, d, J=8.2 Hz), 7.20–7.50 (5H, m)

Reference Example 8

3',5'-Dichloro-4'-hydroxyphenacyl bromide

To a solution of 4-acetyl-2,6-dichlorophenol (157 mg) in tetrahydrofuran (4 ml) were added pyrrolidone hydrotribromide (418 mg) and a catalytic amount of concentrated sulfuric acid, and the mixture was stirred for 5.5 hours at room temperature. The reaction mixture was poured into ice-water and extracted with ethyl acetate. The extract was washed with brine and dried over anhydrous magnesium sulfate. After the solvent was removed under reduced pressure, purification of the residue by flash column chromatography on silica gel (eluent: hexane/ethyl acetate=3/1) gave 3',5'-dichloro-4'-hydroxyphenacyl bromide (197 mg).

$^1$H-NMR(CDCl$_3$) δ ppm: 4.34 (2H, s), 6.33 (1H, br s), 7.94 (2H, s)

Reference Example 9

3'-Fluoro-4-hydroxyphenacyl bromide

To a stirred suspension of aluminum chloride (17.8 g) in 1,2-dichloroethane (149 ml) was added bromoacetyl bromide (3.88 ml) under ice-cooling, and the mixture was stirred for 30 minutes. 2-Fluoroanisole (5.0 ml) was added to the reaction mixture, and the mixture was stirred for 12 hours at room temperature. The reaction mixture was poured into ice-water and extracted with dichloromethane. The extract was washed with brine and dried over anhydrous magnesium sulfate. After the solvent was removed under reduced pressure, purification of the residue by medium pressure liquid column chromatography on silica gel (eluent: hexane/ethyl acetate 5/1) gave 4'-(2-bromoacetoxy)-3'-fluorophenacyl bromide (4.13 g) and 3'-fluoro-4'-hydroxyphenacyl bromide containing impurities (2.57 g). To a solution of the obtained 4'-(2-bromoacetoxy)-3'-fluorophenacyl bromide (4.13 g) in ethanol (58.3 ml) was added 2N aqueous sodium hydroxide solution (6.0 ml) and the mixture was stirred for 25 minutes at room temperature. To the reaction mixture was added 2N hydrochloric acid (6.0 ml) and the mixture was concentrated under reduced pressure. Purification of the residue and the above-mentioned impure 3'-fluoro-4'-hydroxyphenacyl bromide by medium pressure liquid column chromatography on silica gel (eluent: hexane/ethyl acetate=5/1) gave 3'-fluoro-4'-hydroxyphenacyl bromide (4.78 g).

$^1$H-NMR(CDCl$_3$) δ ppm: 4.37 (2H, s), 5.85 (1H, br), 7.10 (1H, t, J=8.4 Hz), 7.70–7.85 (2H, m)

Reference Example 10

4-(2-Bromoethyl)-2,6-dichlorophenol

To a solution of 3',5'-dichloro-4'-hydroxyphenacyl bromide (186 mg) in trifluoroacetic acid (507 μl) was added triethylsilane (345 μl), and the mixture was stirred for 12 hours at room temperature. After concentration of the reaction mixture under reduced pressure, purification of the residue by medium pressure liquid column chromatography on silica gel (eluent: hexane/ethyl acetate=12/1) gave 4-(2-bromoethyl)-2,6-dichlorophenol (104 mg).

$^1$H-NMR(CDCl$_3$) δ ppm: 3.06 (2H, t, J=7.3 Hz), 3.52 (2H, t, J=7.3 Hz), 5.78 (1H, br s), 7.13 (2H, s)

Reference Example 11

The following compound was prepared according to a similar manner to that described in Reference Example 10 using the corresponding phenacyl bromide derivative.

4-(2-Bromoethyl)-2-fluorophenol $^1$H-NMR(CDCl$_3$) δ ppm: 3.08 (2H, t, J=7.4 Hz), 3.52 (2H, t, J=7.4 Hz), 4.70 (1H, br), 6.85–7.00 (3H, m)

Reference Example 12

5'-(2-Bromoethyl)-2'-hydroxyformanilide

To a solution of 4-hydroxyphenethyl alcohol (4.28 g) in acetic acid (40 ml) was added nitric acid (2.6 ml), and the mixture was stirred for 40 minutes at room temperature. After concentration of the reaction mixture under reduced pressure, water was added to the residue and the resulting mixture was extracted with ethyl acetate. The extract was washed with brine and dried over anhydrous magnesium sulfate. Removal of the solvent under reduced pressure gave 4'-hydroxy-3'-nitrophenethyl alcohol (5.38 g). To a solution of the obtained 4'-hydroxy-3'-nitrophenethyl alcohol (2.62 g) in N,N-dimethylformamide (30 ml) were added potassium carbonate (2.17 g) and benzyl bromide (2.0 ml), and the mixture was stirred for 12 hours at room temperature.

The reaction mixture was poured into water and extracted with a mixed solution of diethyl ether and ethyl acetate (9/1). The extract was washed with water and brine, and dried over anhydrous magnesium sulfate. After the solvent was removed under reduced pressure, purification of the residue by flash column chromatography on silica gel (eluent:diethyl ether/dichloromethane=1/1) gave 4'-benzyloxy-3'-nitrophenethyl alcohol (3.31 g).

$^1$H-NMR(CDCl$_3$) δ ppm: 1.42 (1H, br), 2.85 (2H, t, J=6.4 Hz), 3.87 (2H, t, J=6.4 Hz), 5.22 (2H, s), 7.06 (1H, d, J=8.6 Hz), 7.30–7.50 (6H, m), 7.74 (1H, d, J=2.2 Hz)

To a solution of 4'-benzyloxy-3'-nitrophenethyl alcohol (2.17 g) in dichloromethane (30 ml) were added carbon tetrabromide (2.90 g) and triphenylphosphine (2.08 g), and the mixture was stirred for 2.5 hours at room temperature. After concentration of the reaction mixture under reduced pressure, purification of the residue by flash column chromatography on silica gel (eluent: hexane/ethyl acetate=3/1) gave 4'-benzyloxy-3'-nitrophenethyl bromide (2.12 g).

$^1$H-NMR(CDCl$_3$) δ ppm: 3.15 (2H, t, J=7.1 Hz), 3.55 (2H, t, J=7.1 Hz), 5.23 (2H, s), 7.08 (1H, d, J=8.6 Hz), 7.30–7.50 (6H, m), 7.73 (1H, d, J=2.3 Hz)

To a solution of 4'-benzyloxy-3'-nitrophenethyl bromide (4.32 g) in ethanol (35 ml) were added 2N hydrochloric acid (26 ml) and iron powder (3.0 g), and the mixture was heated under reflux for 30 minutes. After cooling, the insoluble material was filtered off and the filtrate was concentrated under reduced pressure. The residue was basified with 2N aqueous sodium hydroxide solution and extracted with dichloromethane. The extract was washed with brine and dried over anhydrous magnesium sulfate. After the solvent was removed under reduced pressure, the residue was dissolved in dichloromethane (20 ml). A mixed solution of formic acid and acetic anhydride (3/5) (2.0 ml) was added to the solution, and the mixture was stirred for 20 minutes at room temperature. The reaction mixture was poured into a saturated aqueous sodium bicarbonate solution and extracted with dichloromethane. The extract was washed with brine and dried over anhydrous magnesium sulfate. After the solvent was removed under reduced pressure, purification of the residue by flash column chromatography on silica gel (eluent: hexane/ethyl acetate=4/1) gave 2'-benzyloxy-5'-(2-bromoethyl)formanilide (1.25 g).

$^1$H-NMR(CDCl$_3$) δ ppm: 3.00–3.30 (2H, m), 3.50–3.80 (2H, m), 5.00–5.20 (2H, m), 6.85–7.15 (2H, m), 7.30–8.80 (8H, m)

To a solution of 2'-benzyloxy-5'-(2-bromoethyl)formanilide (510 mg) in methanol (8 ml) was added 10% palladium carbon (wet, 50% water) (100 mg), and the mixture was stirred for 45 minutes at room temperature under a hydrogen atmosphere. The catalyst was filtered off, and the solvent of the filtrate was removed under reduced pressure. Purification of the residue by flash column chromatography on silica gel (eluent:methanol/dichloromethane/diethyl ether=1/10/10) gave 5'-(2-bromoethyl)-2'-hydroxyformanilide (339 mg).

$^1$H-NMR(DMSO$_3$) δ ppm: 2.80–3.20 (2H, m), 3.50–3.90 (2H, m), 6.70–7.30 (2H, m), 7.80–8.60 (2H, m), 9.10–10.60 (2H, m)

Reference Example 13

Methyl 2-[4-(2-bromoethyl)-2,6-dichlorophenoxy]acetate

To a solution of 4-(2-bromoethyl)-2,6-dichlorophenol (104 mg) in acetone (1.2 ml) were added potassium carbonate (133 mg) and methyl bromoacetate (73 μl), and the mixture was stirred for 3 hours at room temperature. The insoluble material was filtered off, and the filtrate was concentrated under reduced pressure. Purification of the residue by medium pressure liquid column chromatography on silica gel (eluent: hexane/ethyl acetate=12/1) gave methyl 2-[4-(2-bromoethyl)-2,6-dichlorophenoxy]acetate (82 mg).

$^1$H-NMR(CDCl$_3$) δ ppm: 3.09 (2H, t, J=7.3 Hz), 3.53 (2H, t, J=7.3 Hz), 3.85 (3H, s), 4.63 (2H, s), 7.17 (2H, s)

Reference Example 14

The following compounds were prepared according to a similar manner to that described in Reference Example 13 using the corresponding phenol derivative.

Ethyl 2-[4-(2-bromoethyl)-2-fluorophenoxy]acetate $^1$H-NMR(CDCl$_3$) δ ppm: 1.29 (3H, t, J=7.1 Hz), 3.09 (2H, t, J=7.5 Hz), 3.52 (2H, t, J=7.5 Hz), 4.27 (2H, q, J=7.1 Hz), 4.67 (2H, s), 6.85–7.00 (3H, m)

Ethyl 2-[4-(2-bromoethyl) -2-formylaminophenoxy]acetate $^1$H-NMR(CDCl$_3$) δ ppm: 1.15–1.40 (3H, m), 3.00–3.30 (2H, m), 3.45–3.80 (2H, m), 4.20–4.35 (2H, m), 4.60–4.70 (2H, m), 6.75–7.15 (2H, m), 8.00–8.80 (3H, m)

Reference Example 15

4'-Hydroxy-3'-(trifluoromethyl)phenethyl alcohol

To a stirred solution of 4-bromo-2-(trifluoromethyl)aniline (7.05 g) in ethanol (70 ml) were added 42% aqueous tetrafluoroboric acid (14.1 ml) and isoamyl nitrite (5.5 ml) under ice-cooling, and the mixture was stirred for 30 minutes. To the reaction mixture was added diethyl ether, and collection of the resulting precipitates by filtration gave 4-bromo-2-(trifluoromethyl)benzenediazonium tetrafluoroborate (8.69 g) A solution (80 ml) of the obtained 4-bromo-2-(trifluoromethyl)benzenediazonium tetrafluoroborate (8.69 g) in acetic acid was stirred for 12 hours at 120° C., and the reaction mixture was concentrated under reduced pressure. Water was added to the residue, and the resulting mixture was extracted with ethyl acetate. The extract was washed with brine and dried over anhydrous magnesium sulfate. After the solvent was removed under reduced pressure, purification of the residue by flash column chromatography on silica gel (eluent: hexane/ethyl acetate=2/1) gave 4-bromo-2-(trifluoromethyl)phenol (4.37 g).

$^1$H-NMR(CDCl$_3$) δ ppm: 5.80 (1H, br s), 6.86 (1H, d, J=8.7 Hz), 7.52 (1H, dd, J=8.7, 2.4 Hz), 7.63 (1H, d, J=2.4 Hz)

To a solution of 4-bromo-2-(trifluoromethyl)phenol (4.37 g) in N,N-dimethylformamide (40 ml) were added potassium carbonate (3.75 g) and benzyl bromide (2.59 ml), and the mixture was stirred for 12 hours at room temperature. To the reaction mixture was added water, and the resulting mixture was extracted with ethyl acetate. The extract was washed with water and dried over anhydrous magnesium sulfate. After the solvent was removed under reduced pressure, purification of the residue by flash column chromatography on silica gel (eluent: hexane/ethyl acetate=10/1) gave benzyl 4-bromo-2-(trifluoromethyl)phenyl ether (3.37 g). To a stirred solution of the obtained benzyl 4-bromo-2-(trifluoromethyl)phenyl ether (2.05 g) in diethyl ether (20 ml) was added 1.46M tert-butyl lithium solution in pentane (11.4 ml) at −100° C., and the mixture was stirred for 5 minutes. An excess amount of ethylene oxide was added to the reaction mixture, and the mixture was gradually allowed to warm up to −50° C. After a saturated aqueous ammonium chloride solution was added to the reaction mixture, the resulting mixture was allowed to warm up to room temperature and extracted with ethyl acetate. The extract was washed with brine and dried over anhydrous magnesium sulfate. After the solvent was removed under reduced pressure, purification of the residue by flash column chromatography on silica gel (eluent: hexane/ethyl acetate=2/1) gave 4'-benzyloxy-3'-(trifluoromethyl)phenethyl alcohol (1.46 g).

$^1$H-NMR(CDCl$_3$) δ ppm: 2.83 (2H, t, J=6.5 Hz), 3.54 (2H, t, J=6.5 Hz), 5.17 (2H, s), 6.97 (1H, d, J=8.5 Hz), 7.28–7.48 (7H, m)

To a solution (5 ml) of 4'-benzyloxy-3'-(trifluoromethyl) phenethyl alcohol (328 mg) in ethanol was added 10% palladium carbon (73 mg), and the mixture was stirred for 30 minutes at room temperature under a hydrogen atmosphere. After removal of the catalyst by filtration, removal of the solvent under reduced pressure gave 4'-hydroxy-3'-(trifluoromethyl)phenethyl alcohol (195 mg).

$^1$H-NMR(DMSO-d$_6$) δ ppm: 2.66 (2H, t, J=6.8 Hz), 3.50–3.60 (2H, m), 4.61 (1H, t, J=5.1 Hz), 6.92 (1H, d, J=8.3 Hz) 7.28 (1H, d, J=8.3 Hz), 7.32 (1H, s), 10.25 (1H, s)

Reference Example 16

3'-Ethoxy-4'-hydroxyphenethyl alcohol

To a stirred solution of 3'-ethoxy-4'-hydroxyphenylacetic acid (1.0 g) in tetrahydrofuran (25 ml) was added borane-dimethyl sulfide complex (1.3 ml) at room temperature, and the mixture was heated under reflux for 16 hours with stirring. After addition of methanol (20 ml) to the reaction mixture, the resulting mixture was heated under reflux for an hour with stirring, and the solvent was removed under reduced pressure. The residue was dissolved in ethyl acetate, washed with 1N hydrochloric acid, a saturated aqueous sodium bicarbonate solution and brine subsequently, and dried over anhydrous magnesium sulfate. Removal of the solvent under reduced pressure gave 3'-ethoxy-4'-hydroxyphenethyl alcohol (790 mg).

$^1$H-NMR(CDCl$_3$) δ ppm: 1.39 (1H, t, J=6.2 Hz), 1.44 (3H, t, J=7.0 Hz), 2.79 (2H, t, J=6.2 Hz), 3.82 (2H, q, J=6.2 Hz), 4.11 (2H, q, J=7.0 Hz), 5.67 (1H, s), 6.65–6.75 (2H, m), 6.86 (1H, d, J=8.5 Hz)

Reference Example 17

Ethyl 2-[4-(2-hydroxyethyl)-2-(trifluoromethyl)phenoxy]-acetate

To a solution of 4'-hydroxy-3'-(trifluoromethyl)phenethyl alcohol (173 mg) in N,N-dimethylformamide (2 ml) were added potassium carbonate (176 mg) and ethyl bromoacetate (112 μl), and the mixture was stirred for 1 hour at 50° C. The reaction mixture was poured into ice-water and extracted with ethyl acetate. The extract was washed with water and dried over anhydrous magnesium sulfate. Removal of the solvent under reduced pressure gave ethyl 2-[4-(2-hydroxyethyl)-2-(trifluoromethyl)phenoxy]acetate (268 mg).

$^1$H-NMR(CDCl$_3$) δ ppm: 1.29 (3H, t, J=7.1 Hz), 1.40 (1H, t, J=5.6 Hz), 2.85 (2H, t, J=6.5 Hz), 3.81–3.90 (2H, m), 4.26 (2H, q, J=7.1 Hz), 4.70 (2H, s), 6.83 (1H, d, J=8.4 Hz), 7.34 (1H, dd, J=8.4, 2.1 Hz), 7.46 (1H, d, J=2.1 Hz)

Reference Example 18

The following compounds were prepared according to a similar manner to that described in Reference Example 17 using the corresponding phenol derivative.

Ethyl 2-[4-(2-hydroxyethyl)-2-nitrophenoxy]acetate $^1$H-NMR(CDCl$_3$) δ ppm: 1.29 (3H, t, J=7.1 Hz), 1.58 (1H, br), 2.86 (2H, t, J=6.4 Hz), 3.87 (2H, t, J=6.4 Hz), 4.26 (2H, q, J=7.1 Hz), 4.75 (2H, s), 6.94 (1H, d, J=8.6 Hz), 7.40 (1H, dd, J=8.6, 2.2 Hz), 7.76 (1H, d, J=2.2 Hz)

Ethyl 2-[4-(2-hydroxyethyl)-2-methoxyphenoxy] acetate $^1$H-NMR(CDCl$_3$) δ ppm: 1.29 (3H, t, J=7.1 Hz), 1.40–1.50 (1H, m), 2.81 (2H, t, J=6.5 Hz), 3.80–3.90 (5H, m) 4.26 (2H, q, J=7.1 Hz), 4.66 (2H, s), 6.70–6.85 (3H, m)

Ethyl 2-[4-(2-hydroxyethyl)-3-methoxyphenoxy] acetate $^1$H-NMR(CDCl$_3$) δ ppm: 1.31 (3H, t, J=7.1 Hz), 1.57 (1H, t, J=5.9 Hz), 2.83 (2H, t, J=6.4 Hz), 3.75–3.85 (5H, m), 4.28 (2H, q, J=7.1 Hz), 4.59 (2H, s), 6.37 (1H, dd, J=8.2, 2.5 Hz), 6.55 (1H, d, J=2.5 Hz), 7.50 (1H, d, J=8.2 Hz)

Ethyl 2-[2-ethoxy-4-(2-hydroxyethyl)phenoxy] acetate $^1$H-NMR(CDCl$_3$) δ ppm: 1.29 (3H, t, J=7.1 Hz), 1.38 (1H, t, J=6.3 Hz), 1.45 (3H, t, J=7.0 Hz), 2.80 (2H, t, J=6.3 Hz), 3.83 (2H, q, J=6.3 Hz), 4.10 (2H, q, J=7.0 Hz), 4.25 (2H, q, J=7.1 Hz), 4.65 (2H, s), 6.72 (1H, dd, J=8.1, 2.0 Hz), 6.78 (1H, d, J=2.0 Hz), 6.83 (1H, d, J=8.1 Hz)

Reference Example 19

Ethyl 2-[2-cyano-4-(2-hydroxyethyl)phenoxy] acetate

To a solution of 3'-bromo-4'-hydroxyphenylacetic acid (1.26 g) in ethanol (10 ml) was added concentrated sulfuric acid (50 μl), and the mixture was heated under reflux for 2 hours. After cooling, the reaction mixture was poured into ice-water and extracted with ethyl acetate. The extract was washed with a saturated aqueous sodium bicarbonate solution and brine, and dried over anhydrous magnesium sulfate. Removal of the solvent under reduced pressure gave ethyl 3'-bromo-4'-hydroxyphenylacetate (1.26 g). To a solution of the obtained ethyl 3'-bromo-4'-hydroxyphenylacetate (1.26 g) in N,N-dimethylformamide (15 ml) were added potassium carbonate (850 mg) and benzyl bromide (682 μl), and the mixture was stirred for 3 hours at 60° C. The reaction mixture was poured into ice-water and extracted with ethyl acetate. The extract was washed with water and brine, and dried over anhydrous magnesium sulfate. Removal of the solvent under reduced pressure gave ethyl 4'-benzyloxy-3'-bromophenylacetate (1.72 g). To a stirred solution (10 ml) of lithium aluminum hydride (201 mg) in tetrahydrofuran was added a solution of ethyl 4'-benzyloxy-3'-bromophenylacetate (1.72 g) in tetrahydrofuran (10 ml) under ice-cooling, and the mixture was stirred for 30 minutes. To the reaction mixture were added water and a saturated aqueous potassium hydrogensulfate solution, and the resulting mixture was extracted with diethyl ether. The extract was washed with brine and dried over anhydrous magnesium sulfate. After the solvent was removed under reduced pressure, purification of the residue by flash column chromatography on silica gel (eluent: dichloromethane) gave 4'-benzyloxy-3'-bromophenethyl alcohol (837 mg).

To a stirred solution of the obtained 4'-benzyloxy-3'-bromophenethyl alcohol (782 mg) in dichloromethane (8 ml) were added N,N-diisopropylethylamine (665 μl) and chloromethyl methyl ether (232 μl) under ice-cooling, and the mixture was stirred for 6 hours at room temperature. The reaction mixture was poured into water and extracted with ethyl acetate. After the extract was washed with brine, removal of the solvent under reduced pressure gave benzyl 2-bromo-4-(2-methoxymethoxyethyl)phenyl ether (804 mg). To a solution of benzyl 2-bromo-4-(2-methoxymethoxyethyl)phenyl ether (804 mg) in N,N-dimethylformamide (5 ml) was added copper(I) cyanide (458 mg) and the mixture was stirred for 2 days at 120° C. The reaction mixture was poured into water and extracted with ethyl acetate. The extract was washed with brine, and removal of the solvent under reduced pressure gave 2-benzyloxy-5-(2-methoxymethoxyethyl)benzonitrile (711 mg).

$^1$H-NMR(CDCl$_3$) δ ppm: 2.83 (2H, t, J=6.5 Hz), 3.26 (3H, s), 3.71 (2H, t, J=6.5 Hz), 4.59 (2H, s), 5.20 (2H, s), 6.92 (1H, d, J=8.7 Hz), 7.30–7.48 (7H, m)

To a solution of 2-benzyloxy-5-(2-methoxymethoxyethyl) benzonitrile (711 mg) in ethyl acetate (10 ml) was added 10% palladium carbon (100 mg), and the mixture was stirred for 30 minutes at room temperature under a hydrogen atmosphere. After removal of the catalyst by filtration, removal of the solvent under reduced pressure gave 2-hydroxy-5-(2-methoxymethoxyethyl)benzonitrile (496 mg).

$^1$H-NMR(CDCl$_3$) δ ppm: 2.83 (2H, t, J=6.5 Hz), 3.29 (3H, s), 3.72 (2H, t, J=6.5 Hz), 4.61 (2H, s), 6.89 (1H, d, J=8.5 Hz), 7.34 (1H, dd, J=8.5, 2.1 Hz), 7.37 (1H, d, J=2.1 Hz)

To a solution of 2-hydroxy-5-(2-methoxymethoxyethyl) benzonitrile (496 mg) in N,N-dimethylformamide (5 ml) were added potassium carbonate (435 mg) and ethyl bromoacetate (292 μl), and the mixture was stirred for 2 hours at room temperature. The reaction mixture was poured into water and extracted with ethyl acetate. The extract was washed with brine, and removal of the solvent under reduced pressure gave ethyl 2-[2-cyano-4-(2-methoxymethoxyethyl) phenoxy]acetate (619 mg). To a solution of the obtained ethyl 2-[2-cyano-4-(2-methoxymethoxyethyl)phenoxy] acetate (522 mg) in ethanol (5 ml) was added concentrated hydrochloric acid (20 μl), and the mixture was stirred for 2 hours at 70° C. The reaction mixture was poured into water and extracted with ethyl acetate. The extract was washed with brine, and removal of the solvent under reduced pressure gave ethyl 2-[2-cyano-4-(2-hydroxyethyl)phenoxy] acetate (449 mg).

$^1$H-NMR(CDCl$_3$) δ ppm: 1.30 (3H, t, J=7.1 Hz), 1.60 (1H, br), 2.82 (2H, t, J=6.4 Hz), 3.84 (2H, t, J=6.4 Hz), 4.27 (2H, q, J=7.1 Hz), 4.74 (2H, s), 6.79 (1H, d, J=8.6 Hz), 7.38 (1H, dd, J=8.6, 2.1 Hz), 7.47 (1H, d, J=2.1 Hz)

Reference Example 20

Ethyl 2-[5-chloro-4-(2-hydroxyethyl)-2-methoxyphenoxy]acetate

To a solution of 5-chloro-2-methoxyphenol (488 mg) in acetone (15 ml) were added cesium carbonate (1.20 g) and ethyl bromoacetate (375 μl), and the mixture was stirred for 1 hour at room temperature. The insoluble material was filtered off, and the filtrate was concentrated under reduced pressure. Purification of the residue by flash column chromatography on silica gel (eluent: hexane/ethyl acetate=6/1) gave ethyl 2-(5-chloro-2-methoxyphenoxy)acetate (572 mg).

$^1$H-NMR(CDCl$_3$) δ ppm: 1.30 (3H, t, J=7.1 Hz), 3.87 (3H, s), 4.28 (2H, q, J=7.1 Hz), 4.67 (2H, s), 6.81 (1H, d, J=2.4 Hz), 6.82 (1H, d, J=8.7 Hz), 6.95 (1H, dd, J=8.7, 2.4 Hz)

To a stirred solution of ethyl 2-(5-chloro-2-methoxyphenoxy)acetate (606 mg) in trifluoroacetic acid (12 ml) was added hexamethylenetetramine (382 mg) at room temperature, and the mixture was stirred for 9 hours at 60° C. After concentration of the reaction mixture under reduced pressure, a saturated aqueous sodium bicarbonate solution was added to the residue, and the resulting mixture was extracted with ethyl acetate. The extract was washed with water and dried over anhydrous magnesium sulfate. After the solvent was removed under reduced pressure, purification of the residue by flash column chromatography on silica gel (eluent: hexane/ethyl acetate=6/1) gave ethyl 2-(5-chloro-4-formyl-2-methoxyphenoxy)acetate (354 mg).

$^1$H-NMR(CDCl$_3$) δ ppm: 1.31 (3H, t, J=7.1 Hz), 3.93 (3H, s), 4.30 (2H, q, J=7.1 Hz), 4.76 (2H, s), 6.79 (1H, s), 7.43 (1H, s), 10.32 (1H, s)

To a solution of sodium hydride (35 mg) in dimethyl sulfoxide (6 ml) was added trimethylsulfoxonium iodide (335 mg) and the mixture was stirred for 30 minutes at room temperature under an argon atmosphere. To the stirred reaction mixture was added dropwise a solution of ethyl 2-(5-chloro-4-formyl-2-methoxyphenoxy) acetate (346 mg) in dimethyl sulfoxide (5 ml) at room temperature, and the mixture was stirred for 50 minutes. To the reaction mixture was added water, and the resulting mixture was extracted with ethyl acetate. The extract was washed with water and dried over anhydrous magnesium sulfate. After the solvent was removed under reduced pressure, purification of the residue by flash column chromatography on silica gel (eluent: hexane/ethyl acetate=6/1) gave ethyl 2-(5-chloro-2-methoxy-4-oxiranylphenoxy)acetate (135 mg).

$^1$H-NMR(CDCl$_3$) δ ppm: 1.30 (3H, t, J=7.1 Hz), 2.64 (1H, dd, J=5.6, 2.6 Hz), 3.17 (1H, dd, J=5.6, 4.1 Hz), 3.86 (3H, s), 4.10–4.20 (1H, m), 4.27 (2H, q, J=7.1 Hz), 4.66 (2H, s), 6.75 (1H, s), 6.82 (1H, s)

To a solution of ethyl 2-(5-chloro-2-methoxy-4-oxiranylphenoxy)acetate (129 mg) in ethyl acetate (2.5 ml) was added 10% palladium carbon (13 mg), and the mixture was stirred for 3 hours at room temperature under a hydrogen atmosphere. The catalyst was filtered off, and the filtrate was concentrated under reduced pressure. Purification of the residue by flash column chromatography on silica gel (eluent: hexane/ethyl acetate=1/1) gave ethyl 2-[5-chloro-4-(2-hydroxyethyl)-2-methoxyphenoxy]acetate (86 mg).

$^1$H-NMR(CDCl$_3$) δ ppm: 1.30 (3H, t, J=7.1 Hz), 1.35–1.45 (1H, m), 2.94 (2H, t, J=6.6 Hz), 3.80–3.95 (5H, m), 4.27 (2H, q, J=7.1 Hz), 4.65 (2H, s), 6.80 (1H, s), 6.84 (1H, s)

Reference Example 21

Ethyl 2-[5-chloro-2-ethoxy-4-(2-hydroxyethyl) phenoxy]acetate

To a stirred solution of ethyl 2-[2-ethoxy-4-(2-hydroxyethyl)phenoxy]acetate (1.15 g) in dichloromethane (4.3 ml) was added tert-butyl hypochlorite (478 μl) at room temperature, and the mixture was stirred for 15 minutes. To the reaction mixture was added a solution of sodium sulfite (542 mg) in water (5 ml), and the resulting mixture was stirred for 10 minutes at room temperature. The mixture was extracted with ethyl acetate, and the organic layer was washed with brine and dried over anhydrous magnesium sulfate. Removal of the solvent under reduced pressure gave ethyl 2-[5-chloro-2-ethoxy-4-(2-hydroxyethyl)phenoxy] acetate (1.28 g).

$^1$H-NMR(CDCl$_3$) δ ppm: 1.30 (3H, t, J=7.1 Hz), 1.44 (3H, t, J=7.0 Hz), 2.92 (2H, t, J=6.6 Hz), 3.84 (2H, t, J=6.6

Hz), 4.08 (2H, q, J=7.0 Hz), 4.27 (2H, q, J=7.1 Hz), 4.65 (2H, s), 6.80 (1H, s), 6.87 (1H, s)

Reference Example 22

Ethyl 2-[4-(2-bromoethyl)-2-(trifluoromethyl)phenoxy]acetate

To a solution of ethyl 2-[4-(2-hydroxyethyl)-2-(trifluoromethyl)phenoxy]acetate (224 mg) in dichloromethane (2 ml) were added triphenylphosphine (260 mg) and carbon tetrabromide (396 mg), and the mixture was stirred for 30 minutes at room temperature. The reaction mixture was poured into a saturated aqueous sodium bicarbonate solution and extracted with dichloromethane. The extract was washed with water and dried over anhydrous magnesium sulfate. After the solvent was removed under reduced pressure, purification of the residue by flash column chromatography on silica gel (eluent:dichloro-methane/hexane=1/1) gave ethyl 2-[4-(2-bromoethyl)-2-(trifluoromethyl)phenoxy]acetate (178 mg).

$^1$H-NMR(CDCl$_3$) δ ppm: 1.28 (3H, t, J=7.2 Hz), 3.14 (2H, t, J=7.4 Hz), 3.54 (2H, t, J=7.4 Hz), 4.26 (2H, q, J=7.2 Hz), 4.71 (2H, s), 6.84 (1H, d, J=8.5 Hz), 7.32 (1H, dd, J=8.5, 2.1 Hz), 7.44 (1H, d, J=2.1 Hz)

Reference Example 23

The following compounds were prepared according to a similar manner to that described in Reference Example 22 using the corresponding hydroxyethyl derivative.

Ethyl 2-[4-(2-bromoethyl)-2-chlorophenoxy]acetate $^1$H-NMR(CDCl$_3$) δ ppm: 1.29 (3H, t, J=7.1 Hz), 3.08 (2H, t, J=7.5 Hz), 3.54 (2H, t, J=7.5 Hz), 4.27 (2H, q, J=7.1 Hz), 4.69 (2H, s), 6.80 (1H, d, J=8.4 Hz), 7.04 (1H, dd, J=8.4, 2.2 Hz), 7.25 (1H, d, J=2.2 Hz)

Ethyl 2-[4-(2-bromoethyl)-2-nitrophenoxy]acetate $^1$H-NMR(CDCl$_3$) δ ppm: 1.29 (3H, t, J=7.1 Hz), 3.17 (2H, t, J=7.1 Hz), 3.56 (2H, t, J=7.1 Hz), 4.27 (2H, q, J=7.1 Hz), 4.77 (2H, s), 6.95 (1H, d, J=8.6 Hz), 7.38 (1H, dd, J=8.6, 2.3 Hz), 7.75 (1H, d, J=2.3 Hz)

Ethyl 2-[4-(2-bromoethyl)-2-cyanophenoxy]acetate $^1$H-NMR(CDCl$_3$) δ ppm: 1.29 (3H, t, J=7.1 Hz), 3.12 (2H, t, J=7.1 Hz) 3.53 (2H, t, J=7.1 Hz), 4.27 (2H, q, J=7.1 Hz), 4.75 (2H, s), 6.81 (1H, d, J=8.7 Hz), 7.36 (1H, dd, J=8.7, 2.3 Hz), 7.45 (1H, d, J=2.3 Hz)

Ethyl 2-[4-(2-bromoethyl)-5-chloro-2-methoxyphenoxy]acetate $^1$H-NMR(CDCl$_3$) δ ppm: 1.30 (3H, t, J=7.1 Hz), 3.21 (2H, t, J=7.6 Hz), 3.56 (2H, t, J=7.6 Hz), 3.88 (3H, s), 4.27 (2H, q, J=7.1 Hz), 4.65 (2H, s), 6.78 (1H, s), 6.83 (1H, s)

Ethyl 2-[4-(2-bromoethyl)-3-methoxyphenoxy]acetate $^1$H-NMR(CDCl$_3$) δ ppm: 1.30 (3H, t, J=7.1 Hz), 3.09 (2H, t, J=7.7 Hz), 3.52 (2H, t, J=7.7 Hz), 3.80 (3H, s), 4.28 (2H, q, J=7.1 Hz), 4.60 (2H, s), 6.36 (1H, dd, J=8.3, 2.4 Hz), 6.53 (1H, d, J=2.4 Hz), 7.03 (1H, d, J=8.3 Hz)

Ethyl 2-[4-(2-bromoethyl)-5-chloro-2-ethoxyphenoxy]acetate $^1$H-NMR(CDCl$_3$) δ ppm: 1.30 (3H, t, J=7.1 Hz), 1.44 (3H, t, J=7.0 Hz), 3.19 (2H, t, J=7.5 Hz), 3.55 (2H, t, J=7.5 Hz), 4.09 (2H, q, J=7.0 Hz), 4.27 (2H, q, J=7.1 Hz), 4.65 (2H, s), 6.78 (1H, s), 6.86 (1H, s)

Reference Example 24

Ethyl 2-[4-(2-bromoethyl)-2-chloro-5-methoxyphenoxy]acetate

To a stirred solution of ethyl 2-[4-(2-bromoethyl)-3-methoxyphenoxy]acetate (640 mg) in dichloromethane (4 ml) was added tert-butyl hypochlorite (251 μl) at room temperature, and the mixture was stirred for 30 minutes. To the reaction mixture was added a solution of sodium sulfite (504 mg) in water (2 ml) and the resulting mixture was stirred for 30 minutes at room temperature. The mixture was extracted with ethyl acetate. The organic layer was washed with brine and dried over anhydrous magnesium sulfate. After the solvent was removed under reduced pressure, purification of the residue by medium pressure liquid column chromatography on silica gel (eluent: hexane/ethyl acetate=7/1) gave ethyl 2-[4-(2-bromoethyl)-2-chloro-5-methoxyphenoxy]acetate (685 mg).

$^1$H-NMR(CDCl$_3$) δ ppm: 1.30 (3H, t, J=7.1 Hz), 3.07 (2H, t, J=7.6 Hz), 3.51 (2H, t, J=7.6 Hz), 3.79 (3H, s), 4.28 (2H, q, J=7.1 Hz), 4.69 (2H, s), 6.47 (1H, s), 7.15 (1H, s)

Reference Example 25

Ethyl 2-[4-(2-bromoethyl)-2-carbamoylphenoxy]acetate

To a solution of 5-formylsalicylic acid (2.5 g) in methanol (25 ml) was added a catalytic amount of concentrated sulfuric acid, and the mixture was heated under reflux for 17 hours with stirring. After concentration of the reaction mixture under reduced pressure, water was added to the residue, and the resulting mixture was extracted with dichloromethane. The extract was washed with water and dried over anhydrous magnesium sulfate. After the solvent was removed under reduced pressure, the residue was dissolved in N,N-dimethylformamide (20 ml). To the solution were added potassium carbonate (2.29 g) and benzyl bromide (2.0 ml). After the mixture was stirred for 1 hour at 60° C., water was added to the reaction mixture and the resulting mixture was extracted with diethyl ether. The extract was washed with water and brine subsequently, and dried over anhydrous magnesium sulfate. After the solvent was removed under reduced pressure, purification of the residue by flash column chromatography on silica gel (eluent: hexane/ethyl acetate= 4/1) gave methyl 2-benzyloxy-5-formylbenzoate (3.78 g).

To a stirred suspension of methyltriphenylphosphonium bromide (4.1 g) in tetrahydrofuran (40 ml) was added 1.56M n-butyl lithium solution in hexane (7.2 ml) at room temperature, and the mixture was stirred for 1 hour. After the reaction mixture was cooled to −70° C., a solution of methyl 2-benzyloxy-5-formylbenzoate (2.82 g) in tetrahydrofuran (40 ml) was added, and the resulting mixture was stirred for 15 hours with gradually warming up to room temperature. To the reaction mixture was added water, and the resulting mixture was extracted with ethyl acetate. The extract was washed with brine and dried over anhydrous magnesium sulfate. After the solvent was removed under reduced pressure, purification of the residue by flash column chromatography on silica gel (eluent: hexane/ethyl acetate=4/1) gave methyl 2-benzyloxy-5-vinylbenzoate (2.63 g).

To a stirred solution of the obtained methyl 2-benzyloxy-5-vinylbenzoate (1.52 g) in tetrahydrofuran (15 ml) was added dropwise a solution of 9-borabicyclo[3.3.1]nonane (726 mg) in tetrahydrofuran (15 ml) at −20° C., and the mixture was stirred for 17.5 hours at room temperature. After the reaction mixture was cooled to 0° C., 2N aqueous sodium hydroxide solution (8.5 ml) and 30% aqueous hydrogen peroxide solution (6.8 ml) were added to the mixture, and the resulting mixture was stirred for 3 hours at room temperature. To the reaction mixture was added water, and the resulting mixture was extracted with ethyl acetate. The extract was washed with brine and dried over anhydrous magnesium sulfate. After the solvent was removed under reduced pressure, purification of the residue by flash column chromatography on silica gel (eluent: hexane/ethyl acetate= 3/2) gave methyl 2-benzyloxy-5-(2-hydroxyethyl)benzoate (1.30 g).

$^1$H-NMR(CDCl$_3$) δ ppm: 2.83 (2H, t, J=6.5 Hz), 3.85 (2H, t, J=6.5 Hz), 3.91 (3H, s), 5.17 (2H, s), 6.96 (1H, d, J=8.5 Hz), 7.25–7.55 (6H, m), 7.69 (1H, d, J=2.4 Hz)

To a stirred solution of methyl 2-benzyloxy-5-(2-hydroxyethyl)benzoate (1.43 g) in dichloromethane (20 ml) were added N,N-diisopropylethylamine (1.0 ml) and chloromethyl methyl ether (460 μl) under ice-cooling, and the mixture was stirred for 17 hours at room temperature. To the reaction mixture was added a saturated aqueous ammonium chloride solution, and the resulting mixture was extracted with dichloromethane. The extract was washed with brine and dried over anhydrous magnesium sulfate. After the solvent was removed under reduced pressure, purification of the residue by flash column chromatography on silica gel (eluent: hexane/ethyl acetate=4/3) gave methyl 2-benzyloxy-5-(2-methoxymethoxyethyl)benzoate (1.19 g).

To a solution of methyl 2-benzyloxy-5-(2-methoxymethoxyethyl)benzoate (1.34 g) in methanol (15 ml) was added 2N aqueous sodium hydroxide solution (4.0 ml), and the mixture was heated under reflux for 40 minutes with stirring. After the reaction mixture was cooled to 0° C. 2N hydrochloric acid (5.0 ml) was added and the resulting mixture was extracted with dichloromethane. The extract was washed with brine and dried over anhydrous magnesium sulfate. After the solvent was removed under reduced pressure, crystallization of the residue from hexane and diethyl ether (1/1) gave 2-benzyloxy-5-(2methoxymethoxyethyl)benzoic acid (1.23 g).

To a stirred solution of 2-benzyloxy-5-(2-methoxymethoxyethyl)benzoic acid (900 mg) in tetrahydrofuran (25 ml) was added 1,1'-carbonyldiimidazole (507 mg) at room temperature, and the mixture was stirred for 1 hour. To the reaction mixture was added 28% ammonium hydroxide (3 ml), and the resulting mixture was stirred for 30 minutes at room temperature. Water was added to the reaction mixture, and the resulting mixture was extracted with ethyl acetate. The extract was washed with brine and dried over anhydrous magnesium sulfate. After the solvent was removed under reduced pressure, crystallization of the residue from hexane and diethyl ether (1/1) gave 2-benzyloxy-5-(2-methoxymethoxyethyl)benzamide (700 mg).

To a solution of 2-benzyloxy-5-(2-methoxymethoxyethyl) benzamide (721 mg) in methanol (10 ml) was added concentrated hydrochloric acid (0.7 ml), and the mixture was heated under reflux for 1 hour with stirring. Water was added to the reaction mixture, and the resulting mixture was extracted with ethyl acetate. The extract was washed with brine and dried over anhydrous magnesium sulfate. After the solvent was removed under reduced pressure, diethyl ether was added to the residue, and the resulting insoluble material was collected by filtration to give 2-benzyloxy-5-(2-hydroxyethyl)benzamide (519 mg).

$^1$H-NMR(CDCl$_3$) δ ppm: 1.45 (1H, t, J=5.8 Hz), 2.87 (2H, t, J=6.5 Hz), 3.80–3.95 (2H, m), 5.18 (2H, s), 5.71 (1H, br), 7.02 (1H, d, J=8.4 Hz), 7.30–7.50 (6H, m), 7.77 (1H, br), 8.11 (1H, d, J=2.4 Hz)

To a solution of 2-benzyloxy-5-(2-hydroxyethyl) benzamide (519 mg) in dichloromethane (6 ml) were added triethylamine (290 μl), N,N-dimethylaminopyridine (24 mg) and p-toluenesulfonyl chloride (400 mg) subsequently, and the mixture was stirred for 17 hours at room temperature. After concentration of the reaction mixture under reduced pressure, purification of the residue by flash column chromatography on silica gel (eluent:diethyl ether/ dichloromethane=1/1) gave 2-benzyloxy-5-[2-(p-toluenesulfonyloxy)ethyl]benzamide (627 mg).

2-Benzyloxy-5-[2-(p-toluenesulfonyloxy)ethyl] benzamide (627 mg) was dissolved in methanol (5 ml) and tetrahydrofuran (5 ml), and 10% palladium carbon (wet, 50% water) (169 mg) was added to the solution. The mixture was stirred for 1 hour at room temperature under a hydrogen atmosphere, and the catalyst was filtered off. Removal of the solvent under reduced pressure gave 2-hydroxy-5-[2-toluenesulfonyloxy)ethyl]benzamide (465 mg).

To a stirred solution of 2-hydroxy-5-[2-(p-toluenesulfonyloxy)ethyl]benzamide (465 mg) in N,N-dimethylformamide (5 ml) were added potassium carbonate (193 mg) and ethyl bromoacetate (160 μl) at room temperature, and the mixture was stirred for 1.5 hours at 50° C. To the reaction mixture was added water, and the resulting mixture was extracted with ethyl acetate. The extract was washed with water and brine subsequently, and dried over anhydrous magnesium sulfate. After the solvent was removed under reduced pressure, diethyl ether was added to the residue and the resulting insoluble material was collected by filtration to give ethyl 2-[4-(2-bromoethyl)-2-carbamoylphenoxy]acetate (250 mg).

$^1$H-NMR(CDCl$_3$) δ ppm 1.34 (3H, t, J=7.1 Hz), 3.16 (2H, t, J=7.3 Hz), 3.57 (2H, t, J=7.3 Hz), 4.33 (2H, q, J=7.1 Hz), 4.73 (2H, s), 5.81 (1H, br), 6.82 (1H, d, J=8.4 Hz), 7.33 (1H, dd, J=8.4, 2.4 Hz), 8.11 (1H, d, J=2.4 Hz), 8.40 (1H, br)

Reference Example 26

2-[2-Dimethylamino-4-(2-hydroxyethyl)phenoxy]- N,N-dimethylacetamide

To a solution of 4-hydroxyphenethyl alcohol (4.28 g) in acetic acid (40 ml) was added nitric acid (2.6 ml), and the mixture was stirred for 40 minutes at room temperature. After concentration of the reaction mixture under reduced pressure, water was added to the residue, and the resulting mixture was extracted with ethyl acetate. The extract was washed with brine and dried over anhydrous magnesium sulfate. Removal of the solvent under reduced pressure gave 4'-hydroxy-3'-nitrophenethyl alcohol (5.38 g).

To a solution of 4'-hydroxy-3'-nitrophenethyl alcohol (6.00 g) in acetone (72.6 ml) were added potassium carbonate (7.52 g) and 2-bromo-N,N-dimethylacetamide (4.25 ml), and the mixture was stirred for 20 hours at room temperature. The insoluble material was filtered off, and the filtrate was concentrated under reduced pressure. The residue was dissolved in ethyl acetate, washed with water and brine, and dried over anhydrous magnesium sulfate. After removal of the solvent under reduced pressure, crystallization of the residue from ethyl acetate gave 2-[4-(2-hydroxyethyl)-2-nitrophenoxy]-N,N-dimethylacetamide (1.77 g).

$^1$H-NMR(CDCl$_3$) δ ppm: 1.60–1.75 (1H, m), 2.85 (2H, t, J=6.4 Hz), 2.97 (3H, s), 3.13 (3H, s), 3.80–3.90 (2H, m), 4.83 (2H, s), 7.12 (1H, d, J=8.6 Hz), 7.39 (1H, dd, J=8.6, 2.2 Hz), 7.74 (1H, d, J=2.2 Hz)

To a solution of 2-[4-(2-hydroxyethyl)-2-nitrophenoxy]-N,N-dimethylacetamide (1.66 g) in ethanol (8.3 ml) were added 37% aqueous formaldehyde solution (1.66 ml) and 10% palladium carbon (166 mg), and the mixture was stirred for 20 hours at room temperature under a hydrogen atmosphere (5 kgf/cm$^2$). The catalyst was filtered off, and the solvent was removed under reduced pressure. Purification of the residue by medium pressure liquid column chromatography on silica gel (eluent:dichloromethane/methanol=15/1) gave 2-[2-dimethylamino-4-(2-hydroxyethyl)phenoxy]-N,N-dimethylacetamide (1.98 g).

$^1$H-NMR(CDCl$_3$) δ ppm: 2.75–2.85 (8H, m), 2.99 (3H, s), 3.10 (3H, s), 3.75–3.90 (2H, m), 4.75 (2H, s), 6.70–6.85 (3H, m)

Reference Example 27

Ethyl 2-[2-methoxy-4-[2-(p-toluenesulfonyloxy) ethyl]phenoxy]acetate

To a solution of ethyl 2-[4-(2-hydroxyethyl)-2-methoxyphenoxy]acetate (1.53 g) in dichloromethane (30 ml) were added triethylamine (1.26 ml) and p-toluenesulfonyl chloride (1.26 g), and the mixture was stirred for 24 hours at room temperature. The reaction mixture was washed with 1N hydrochloric acid and brine, and dried over anhydrous magnesium sulfate. After the solvent was removed under reduced pressure, purification of the residue by medium pressure liquid column chromatography on silica gel (eluent: hexane/ethyl acetate=3/2) gave ethyl 2-[2-methoxy-4-[2-(p-toluenesulfonyloxy)ethyl] phenoxy]acetate (2.04 g).

$^1$H-NMR(CDCl$_3$) δ ppm: 1.29 (3H, t, J=7.1 Hz), 2.43 (3H, s), 2.89 (2H, t, J=6.9 Hz), 3.80 (3H, s), 4.19 (2H, t, J=6.9 Hz), 4.25 (2H, q, J=7.1 Hz), 4.64 (2H, s), 6.55–6.65 (2H, m), 6.70–6.75 (1H, m), 7.25–7.35 (2H, m), 7.65–7.70 (2H, m)

Reference Example 28

The following compound was prepared according to a similar manner to that described in Reference Example 27 using N,N-dimethyl-2-[2-dimethylamino-4-(2-hydroxyethyl)phenoxy]acetamide instead of ethyl 2-[4-(2-hydroxyethyl)-2-methoxyphenoxy]acetate.

N,N-Dimethyl-2-[2-dimethylamino-4-[2-(p-toluenesulfonyloxy)ethyl]phenoxy]acetamide $^1$H-NMR(CDCl$_3$) δ ppm: 2.44 (3H, s), 2.78 (6H, s), 2.88 (2H, t, J=7.2 Hz), 2.99 (3H, s), 3.09 (3H, s), 4.17 (2H, t, J=7.2 Hz), 4.73 (2H, s), 6.60–6.80 (3H, m), 7.25–7.35 (2H, m), 7.65–7.75 (2H, m)

Reference Example 29

Ethyl 2-[4-(2-bromoethyl)-2-(dimethylaminocarbonyl)phenoxy]acetate

To a stirred solution of methyl 2-benzyloxy-5-vinylbenzoate (1.95 g) in methanol (10 ml) was added 2N aqueous sodium hydroxide solution (7.6 ml) at room temperature, and the mixture was heated under reflux for 1 hour with stirring. The reaction mixture was acidified with 2N hydrochloric acid, and the resulting mixture was extracted with dichloromethane. The extract was washed with brine and dried over anhydrous magnesium sulfate, and the solvent was removed under reduced pressure. Crystallization of the residue from a mixed solution of hexane and diethyl ether (2/1) gave 2-benzyloxy-5-vinylbenzoic acid (1.49 g)

$^1$H-NMR(DMSO-d$_6$) δ ppm: 5.19 (1H, d, J=11.0 Hz), 5.22 (2H, s), 5.74 (1H, d, J=17.7 Hz), 6.70 (1H, dd, J=17.7, 11.0 Hz), 7.18 (1H, d, J=8.7 Hz), 7.25–7.55 (5H, m), 7.60 (1H, dd, J=8.7, 2.3 Hz), 7.72 (1H, d, J=2.3 Hz), 12.7 (1H, br s)

To a solution of 2-benzyloxy-5-vinylbenzoic acid (607 mg) in benzene (10 ml) were added thionyl chloride (350 μl) and a catalytic amount of N,N-dimethylformamide, and the mixture was heated under reflux for 1 hour with stirring. After concentration of the reaction mixture under reduced pressure, the residue was dissolved in tetrahydrofuran (5 ml), and an excess amount of 50% aqueous dimethylamine solution was added to the stirred solution under ice-cooling. Water was added to the reaction mixture, and the resulting mixture was extracted with ethyl acetate. The extract was washed with brine and dried over anhydrous magnesium sulfate. After the solvent was removed under reduced pressure, purification of the residue by flash column chromatography on silica gel (eluent:hexane/diethyl ether/dichloromethane=1/2/2) gave 2-benzyloxy-N,N-dimethyl-5-vinylbenzamide (548 mg).

$^1$H-NMR(CDCl$_3$) δ ppm: 2.86 (3H, s), 3.11 (3H, s), 5.12 (2H, s), 5.17 (1H, d, J=10.7 Hz), 5.62 (1H, d, J=17.8 Hz), 6.63 (1H, dd, J=17.8, 10.7 Hz), 6.89 (1H, d, J=8.0 Hz), 7.25–7.45 (7H, m)

To a stirred solution of 2-benzyloxy-N,N-dimethyl-5-vinylbenzamide (560 mg) in tetrahydrofuran (5 ml) was added dropwise a solution of 9-borabicyclo[3.3.1]nonane (255 mg) in tetrahydrofuran (8 ml) at −20° C. under an argon atmosphere, and the mixture was stirred for 14.5 hours at room temperature. To the stirred reaction mixture were added 2N aqueous sodium hydroxide solution (3.0 ml) and 30% aqueous hydrogen peroxide solution (2.4 ml) under ice-cooling, and the resulting mixture was stirred for 5 hours at room temperature. To the reaction mixture was added water, and the resulting mixture was extracted with dichloromethane. The extract was washed with brine and dried over anhydrous magnesium sulfate. After the solvent was removed under reduced pressure, purification of the residue by flash column chromatography on silica gel (eluent:hexane/diethyl ether/dichloromethane=1/2/2 and methanol/diethyl ether/dichloromethane=1/10/10) gave 2-benzyloxy-5-(2-hydroxyethyl)-N,N-dimethylbenzamide (300 mg).

$^1$H-NMR(CDCl$_3$) δ ppm: 2.70–2.90 (5H, m), 3.08 (3H, s), 3.65–3.85 (3H, m), 5.08 (2H, s), 6.80–6.95 (1H, m), 7.05–7.45 (7H, m)

To a stirred solution of 2-benzyloxy-5-(2-hydroxyethyl)-N,N-dimethylbenzamide (300 mg) in dichloromethane (5 ml) were added carbon tetrabromide (366 mg) and triphenylphosphine (289 mg) at room temperature, and the mixture was stirred for minutes. After concentration of the reaction mixture under reduced pressure, purification of the residue by flash column chromatography on silica gel (eluent: hexane/ethyl acetate=3/2) gave 2-benzyloxy-5-(2-bromoethyl)-N,N-dimethylbenzamide (124 mg). $^1$H-NMR (CDCl$_3$) δ ppm: 2.86 (3H, s), 3.00–3.15 (2H, m), 3.11 (3H, s), 3.45–3.60 (2H, m), 5.11 (2H, s), 6.90 (1H, d, J=8.3 Hz), 7.05–7.20 (2H, m), 7.25–7.40 (5H, m)

To a solution of 2-benzyloxy-5-(2-bromoethyl)-N,N-dimethylbenzamide (100 mg) in methanol (3 ml) was added 10% palladium carbon (30 mg), and the mixture was stirred for 15 minutes at room temperature under a hydrogen atmosphere. After removal of the catalyst by filtration, the filtrate was concentrated under reduced pressure and the residue was dissolved in N,N-dimethylformamide (2 ml). To the solution were added potassium carbonate (42 mg) and ethyl bromoacetate (34 μl), and the mixture was stirred for 16 hours at room temperature. The reaction mixture was poured into a dilute hydrochloric acid and extracted with a mixed solution of diethyl ether and ethyl acetate (4/1). The extract was washed with water and brine, and dried over anhydrous magnesium sulfate. After the solvent was removed under reduced pressure, purification of the residue by flash column chromatography on silica gel (eluent:dichloromethane/diethyl ether=1/1) gave ethyl 2-[4-(2-bromoethyl)-2-(dimethylaminocarbonyl)phenoxy] acetate (72 mg).

$^1$H-NMR(CDCl$_3$) δ ppm: 1.28 (3H, t, J=6.3 Hz), 2.92 (3H, s), 3.05–3.15 (5H, m), 3.45–3.60 (2H, m), 4.24 (2H, q, J=6.3 Hz), 4.63 (2H, s), 6.71 (1H, d, J=8.8 Hz), 7.10–7.20 (2H, m)

EXAMPLE 1

Ethyl 2-[2-bromo-4-[2-[[(1S,2R)-2-hydroxy-2-(4-hydroxyphenyl)-1-methylethyl]amino]ethyl] phenoxy]acetate (Compound 1)

A suspension of (1R,2S)-2-amino-1-(4-hydroxyphenyl) propan-1-ol (475 mg), ethyl 2-[2-bromo-4-(2-bromoethyl) phenoxy]acetate (520 mg) and molecular sieves 4A powder (1.42 g) in N,N-dimethylformamide (4.7 ml) was stirred for 2 days at room temperature. Purification of the reaction mixture by medium pressure liquid column chromatography on aminopropyl silica gel (eluent:dichloromethane/methanol=10/1) gave ethyl 2-[2-bromo-4-[2-[[(1S,2R)-2-hydroxy-2-(4-hydroxyphenyl)-1-methylethyl]amino]ethyl] phenoxy]acetate (356 mg).

$^1$H-NMR(DMSO-d$_6$) δ ppm: 0.80 (3H, d, J=6.4 Hz), 1.15–1.30 (4H, m), 2.40–2.80 (5H, m), 4.17 (2H, q, J=7.1 Hz), 4.35–4.45 (1H, m), 4.80–4.90 (3H, m), 6.67 (2H, d, J=8.5 Hz), 6.87 (1H, d, J=8.5 Hz), 7.00–7.15 (3H, m), 7.41 (1H, d, J=2.1 Hz), 9.13 (1H, br)

Specific Rotation: $[α]_D^{25}$=−5.6° (c=0.82, Acetic acid)

EXAMPLE 2

The following compounds were prepared according to a similar manner to that described in Example 1 using the corresponding phenoxyacetic acid derivative.

Ethyl 2-[2-chloro-4-[2-[[(1S,2R)-2-hydroxy-2-(4-hydroxyphenyl)-1-methylethyl]amino]ethyl] phenoxy]acetate (Compound 2)

$^1$H-NMR(CDCl$_3$) δ ppm: 0.98 (3H, d, J=6.4 Hz), 1.33 (3H, t, J=7.1 Hz), 2.60–2.85 (4H, m), 2.90–3.05 (1H, m), 4.31 (2H, q, J=7.1 Hz), 4.47 (1H, d, J=5.6 Hz), 4.69 (2H, s), 6.64–6.75 (3H, m), 6.91 (1H, dd, J=8.4, 2.1 Hz), 7.06 (2H, d, J=8.6 Hz), 7.13 (1H, d, J=2.1 Hz)

Methyl 2-[2,6-dichloro-4-[2-[[(1S,2R)-2-hydroxy-2-(4-hydroxyphenyl)-1-methylethyl]amino]ethyl] phenoxy]acetate (Compound 3)

$^1$H-NMR(CDCl$_3$) δ ppm: 0.95 (3H, d, J=6.4 Hz), 2.60–3.05 (5H, m), 3.87 (3H, s), 4.49 (1H, d, J=5.3 Hz), 4.63 (2H, s), 6.77 (2H, d, J=8.6 Hz), 7.05–7.15 (4H, m)

Ethyl 2-[2,5-dichloro-4-[2-[[(1S,2R)-2-hydroxy-2-(4-hydroxyphenyl)-1-methylethyl]amino]ethyl] phenoxy]acetate (Compound 4)

$^1$H-NMR(CDCl$_3$) δ ppm: 0.96 (3H, d, J=6.4 Hz), 1.33 (3H, t, J=7.1 Hz), 2.70–3.05 (5H, m), 4.32 (2H, q, J=7.1 Hz), 4.53 (1H, d, J=5.2 Hz), 4.68 (2H, s), 6.74 (2H, d, J=8.6 Hz), 6.79 (1H, s), 7.11 (2H, d, J=8.6 Hz), 7.17 (1H, s)

Ethyl 2-[2-fluoro-4-[2-[[(1S,2R)-2-hydroxy-2-(4-hydroxyphenyl)-1-methylethyl]amino]ethyl] phenoxy]acetate (Compound 5)

$^1$H-NMR(DMSO-d$_6$) δ ppm: 0.80 (3H, d, J=6.4 Hz), 1.15–1.30 (4H, m), 2.40–2.80 (5H, m), 4.17 (2H, q, J=7.1 Hz), 4.35–4.45 (1H, m), 4.80–4.90 (3H, m), 6.66 (2H, d, J=8.5 Hz), 6.80–7.10 (5H, m), 9.16 (1H, br)

Specific Rotation: $[α]_D^{24}$=−7.2° (c=0.50, Acetic acid)

Ethyl 2-[4-[2-[[(1S,2R)-2-hydroxy-2-(4-hydroxyphenyl)-1-methylethyl]amino]ethyl]-2-methoxyphenoxy]acetate (Compound 6)

$^1$H-NMR(DMSO-d$_6$) δ ppm: 0.81 (3H, d, J=6.4 Hz), 1.10–1.40 (4H, m), 2.40–2.80 (5H, m), 3.75 (3H, s), 4.15 (2H, q, J=6.9 Hz), 4.30–4.50 (1H, m), 4.67 (2H, s), 4.70–4.90 (1H, m)), 6.55–6.90 (5H, m), 7.06 (2H, d, J=8.4 Hz), 9.15 (1H, br)

Specific Rotation: $[α]_D^{25}$=−7.5° (c=0.67, Acetic acid)

Ethyl 2-[2-ethoxy-4-[2-[[(1S,2R)-2-hydroxy-2-(4-hydroxyphenyl)-1-methylethyl]amino]ethyl] phenoxy]acetate (Compound 7)

$^1$H-NMR(DMSO-d$_6$) δ ppm: 0. 81 (3H, d, J=6. 4 Hz), 1. 20 (3H, t, J=7.0 Hz), 1.32 (3H, t, J=7.0 Hz), 2.50–2.80 (5H, m), 4.00 (2H, q, J=7.0 Hz), 4.15 (2H, q, J=7.0 Hz), 4.39 (1H, br s), 4.69 (2H, s), 4.87 (1H, brs), 6.61 (1H, d, J=8.0 Hz), 6.68 (2H, d, J=8.4 Hz), 6.72 (1H, d, J=8.0 Hz), 6.79 (1H, s), 7.17 (2H, d, J=8.4 Hz), 9.18 (1H, br)

Ethyl 2-[2-benzyloxy-4-[2-[[(1S,2R)-2-hydroxy-2-(4-hydroxyphenyl)-1-methylethyl]amino]ethyl] phenoxy]acetate (Compound 8)

$^1$H-NMR(CD$_3$OD) δ ppm: 1.15 (3H, d, J=6.3 Hz), 1.31 (3H, t, J=7.1 Hz), 2.50–2.80 (4H, m), 2.85–2.95 (1H, m), 4.26 (2H, q, J=7.1 Hz), 4.32 (1H, d, J=6.9 Hz), 4.73 (2H, s), 5.12 (2H, s), 6.57 (1H, dd, J=8.2, 2.0 Hz), 6.71 (2H, d, J=8.5 Hz), 6.79 (1H, d, J=8.2 Hz), 6.81 (1H, d, J=2.0 Hz), 7.05 (2H, d, J=8.5 Hz), 7.30–7.55 (5H, m)

Ethyl 2-[5-chloro-4-[2-[[(1S,2R)-2-hydroxy-2-(4-hydroxyphenyl)-1-methylethyl]amino]ethyl]-2-methoxyphenoxy]acetate (Compound 9)

$^1$-NMR(CDCl$_3$) δ ppm: 0.98 (3H, d, J=6.4 Hz), 1.33 (3H, t, J=7.1 Hz), 2.70–3.05 (5H, m), 3.81 (3H, s), 4.32 (2H, q, J=7.1 Hz), 4.50 (1H, d, J=5.8 Hz), 4.60–4.70 (2H, m), 6.62 (1H, s), 6.72 (2H, d, J=8.5 Hz), 6.75 (1H, s), 7.08 (2H, d, J=8.5 Hz)

Specific Rotation: $[α]_D^{31}$=−10.5° (c=0.21, Acetic acid)

Ethyl 2-[4-[2-[[(1S,2R)-2-hydroxy-2-(4-hydroxyphenyl)-1-methylethyl]amino]ethyl]-2-methylphenoxy]acetate (Compound 10)

$^1$H-NMR(CDCl$_3$) δ ppm: 1.00 (3H, d, J=6.4 Hz), 1.34 (3H, t, J=7.1 Hz), 2.22 (3H, s), 2.55–2.80 (4H, m), 2.90–3.05 (1H, m), 4.32 (2H, q, J=7.1 Hz), 4.45 (1H, d, J=5.9 Hz), 4.64 (2H, s), 6.52 (1H, d, J=8.9 Hz), 6.67 (2H, d, J=8.5 Hz), 6.80–6.90 (2H, m), 7.02 (2H, d, J=8.5 Hz)

Ethyl 2-[2-ethyl-4-[2-[[(1S,2R)-2-hydroxy-2-(4-hydroxyphenyl)-1-methylethyl]amino]ethyl] phenoxy]acetate (Compound 11)

$^1$H-NMR(DMSO-d$_6$) δ ppm: 0.81 (3H, d, J=6.4 Hz), 1.13 (3H, t, J=7.5 Hz), 1.21 (3H, t, J=7.1 Hz), 2.45–2.80 (7H, m), 4.16 (2H, q, J=7.1 Hz), 4.40 (1H, d, J=4.4 Hz), 4.74 (2H, s), 4.86 (1H, br), 6.60–6.75 (3H, m), 6.89 (1H, dd, J=8.3, 2.0 Hz), 6.95 (1H, d, J=2.0 Hz), 7.06 (2H, d, J=8.5 Hz), 9.18 (1H, br)

Ethyl 2-[4-[2-[[(1S,2R)-2-hydroxy-2-(4-hydroxyphenyl)-1-methylethyl]amino]ethyl]-2,5-dimethylphenoxy]acetate (Compound 12)

$^1$H-NMR(CDCl$_3$) δ ppm: 0.98 (3H, d, J=6.4 Hz), 1.34 (3H, t, J=7.1 Hz), 2.18 (3H, s), 2.22 (3H, s), 2.60–3.00 (5H, m), 4.31 (2H, q, J=7.1 Hz), 4.49 (1H, d, J=5.6 Hz), 4.62 (2H, s), 6.41 (1H, s), 6.69 (2H, d, J=8.5 Hz), 6.78 (1H, s), 7.05 (2H, d, J=8.5 Hz)

Ethyl 2-[4-[2-[[(1S,2R)-2-hydroxy-2-(4-hydroxyphenyl)-1-methylethyl]amino]ethyl]-2-(trifluoromethyl)phenoxy]acetate (Compound 13)

$^1$H-NMR(DMSO-d$_6$+D$_2$O) δ ppm: 0.95 (3H, d, J=6.6 Hz), 1.21 (3H, t, J=7.1 Hz), 2.85–3.05 (2H, m), 3.10–3.40 (3H, m), 4.17 (2H, q, J=7.1 Hz), 4.90–5.00 (3H, m), 6.77 (2H, d, J=8.6 Hz), 7.12 (1H, d, J=8.7 Hz), 7.17 (2H, d, J=8.6 Hz), 7.51 (1H, d, J=8.7 Hz), 7.57 (1H, s)

Ethyl 2-[2-cyano-4-[2-[[(1S,2R)-2-hydroxy-2-(4-hydroxyphenyl)-1-methylethyl]amino]ethyl]phenoxy]acetate (Compound 14)

$^1$H-NMR(CDCl$_3$) δ ppm: 1.01 (3H, d, J=6.4 Hz), 1.32 (3H, t, J=7.1 Hz), 2.60–2.85 (4H, m), 2.90–3.05 (1H, m), 4.30 (2H, q, J=7.1 Hz), 4.46 (1H, d, J=5.7 Hz), 4.75 (2H, s), 6.67–6.76 (3H, m), 7.06 (2H, d, J=8.5 Hz), 7.23 (1H, dd, J=8.6, 2.2 Hz), 7.28 (1H, d, J=2.2 Hz)

Ethyl 2-[4-[2-[[(1S,2R)-2-hydroxy-2-(4-hydroxyphenyl)-1-methylethyl]amino]ethyl ]-2-nitrophenoxy]acetate (Compound 15)

$^1$H-NMR(DMSO-d$_6$) δ ppm: 0.94 (3H, d, J=6.7 Hz), 1.20 (3H, t, J=7.1 Hz), 2.90–3.05 (2H, m), 3.10–3.40 (3H, m), 4.16 (2H, q, J=7. 1 Hz), 4.90–5.05 (3H, m), 5.86 (1H, br), 6.76 (2H, d, J=8.5 Hz), 7.16 (2H, d, J=8.5 Hz), 7.27 (1H, d, J=8.7 Hz), 7.53 (1H, dd, J=8.7, 2.0 Hz) 7.83 (1H, d, J=2.0 Hz), 8.45 (1H, br), 9.37 (1H, s)

Ethyl 2-[2-carbamoyl-4-[2-[[(1S,2R)-2-hydroxy-2-(4-hydroxyphenyl)-1-methylethyl]amino]ethyl]phenoxy]acetate (Compound 16)

$^1$H-NMR(DMSO-d$_6$) δ ppm: 0.81 (3H, d, J=6.4 Hz), 1.24 (3H, t, J=7.1 Hz), 2.60–2.85 (5H, m), 4.21 (2H, q, J=7.1 Hz), 4.40–4.50 (1H, m), 4.85–5.05 (3H, m), 6.61 (2H, d, J=8.5 Hz), 6.97 (1H, d, J=8.5 Hz), 7.06 (2H, d, J=8.5 Hz), 7.25 (1H, dd, J=8.5, 2.4 Hz), 7.64 (1H, br s), 7.75 (1H, d, J=2.4 Hz), 7.98 (1H, br s), 9.20 (1H, br)

Ethyl 2-[2-formylamino-4-[2-[[(1S,2R)-2-hydroxy-2-(4-hydroxyphenyl)-1-methylethyl]amino]ethyl]phenoxy]acetate hydrobromide (Compound 17)

$^1$H-NMR(DMSO-d$_6$) δ ppm: 0.85–1.30 (6H, m), 2.80–3.30 (4H, m), 3.30–4.00 (1H, m), 4.00–4.65 (2H, m), 4.80–5.05 (2H, m), 5.20–5.40 (1H, m), 5.80–6.10 (1H, br), 6.60–10.80 (12H, m)

N,N-Dimethyl-2-[2-dimethylamino-4-[2-[[(1S,2R)-2-hydroxy-2-(4-hydroxyphenyl)-1-methylethyl]amino]ethyl]phenoxy]acetamiide (Compound 18)

$^1$H-NMR(DMSO-d$_6$) δ ppm: 0.80 (3H, d, J=6.4 Hz), 1.25 (1H, br), 2.45–2.80 (11H, m), 2.85 (3H, s), 3.00 (3H, s), 4.50 (1H, br), 4.74 (2H, s), 4.85 (1H, br), 6.55–6.70 (5H, m), 7.06 (2H, d, J=8.5 Hz), 9.20 (1H, br)

Ethyl 2-[2-chloro-4-[2-[[(1S,2R)-2-hydroxy-2-(4-hydroxyphenyl)-1-methylethyl]amino]ethyl]-5-methoxyphenoxy]acetate (Compound 19)

$^1$H-NMR(CDCl$_3$) δ ppm: 0.92 (3H, d, J=6.4 Hz), 1.32 (3H, t, J=7.1 Hz), 2.60–3.00 (5H, m), 3.74 (3H, s), 4.31 (2H, q, J=7.1 Hz), 4.53 (1H, d, J=5.1 Hz), 4.69 (2H, s), 6.41 (1H, s), 6.75 (2H, d, J=8.4 Hz), 7.07 (1H, s), 7.10 (2H, d, J=8.4 Hz)

Ethyl 2-[5-chloro-2-ethoxy-4-[2-[[(1S,2R)-2-hydroxy-2-(4-hydroxyphenyl)-1-methylethyl]amino]ethyl]phenoxy]acetate (Compound 20)

$^1$H-NMR(CDCl$_3$) δ ppm: 0.97 (3H, d, J=6.4 Hz), 1.33 (3H, t, J=7.1 Hz), 1.43 (3H, t, J=7.0 Hz), 2.70–3.05 (5H, m), 3.90–4.05 (2H, m), 4.31 (2H, q, J=7.1 Hz), 4.51 (1H, d, J=5.5 Hz), 4.55–4.75 (2H, m), 6.63 (1H, s), 6.71 (2H, d, J=8.5 Hz), 6.79 (1H, s), 7.08 (2H, d, J=8.5 Hz)

Specific Rotation: $[α]_D^{31}$=−6.8° (c=1.00, Acetic acid)

Ethyl 2-[2-(dimethylaminocarbonyl)-4-[2-[[(1S,2R)-2-hydroxy-2-(4-hydroxyphenyl)-1-methylethyl]amino]ethyl]phenoxy]acetate (Compound 21)

$^1$H-NMR(CD$_3$OD) δ ppm: 1.12 (3H, d, J=6.7 Hz), 1.30 (3H, t, J=7.1 Hz), 2.98 (3H, s), 3.03 (2H, t, J=7.5 Hz), 3.13 (3H, s), 3.25–3.50 (3H, m), 4.26 (2H, q, J=7.1 Hz), 4.80 (1H, d, J=7.0 Hz) 4.85–5.10 (2H, m), 6.82 (2H, d, J=8.6 Hz), 6.95 (1H, d, J=8.6 Hz), 7.15–7.30 (3H, m), 7.36 (1H, dd, J=8.6 Hz, 2.2 Hz)

Ethyl 2-[2-chloro-4-[2-[[(1S,2R)-2-hydroxy-2-(4-hydroxyphenyl)-1-methylethyl]amino]ethyl]-5-methylphenoxy]acetate (Compound 22)

$^1$H-NMR(CDCl$_3$) δ ppm: 0.97 (3H, d, J=6.5 Hz) 1.32 (3H, t, J=7.2 Hz), 2.21 (3H, s), 2.50–3.00 (5H, m), 4.30 (2H, q, J=7.2 Hz), 4.53 (1H, d, J=5.3 Hz), 4.67 (2H, s), 6.58 (1H, s), 6.73 (2H, d, J=8.4 Hz), 7.06 (1H, s), 7.08 (2H, d, J=8.4 Hz)

Ethyl 2-[2,5-difluoro-4-[2-[[(1S,2R)-2-hydroxy-2-(4-hydroxyphenyl)-1-methylethyl]amino]ethyl]phenoxy]acetate (Compound 23)

$^1$H-NMR(CDCl$_3$) δ ppm: 0.97 (3H, d, J=6.4 Hz), 1.32 (3H, t, J=7.1 Hz), 2.60–3.00 (5H, m), 4.30 (2H, q, J=7.1 Hz), 4.50 (1H, d, J=5.4 Hz), 4.66 (2H, s), 6.58 (1H, dd, J=10.4, 7.0 Hz), 6.73 (2H, d, J=8.5 Hz), 6.83 (1H, dd, J=11.4, 6.9 Hz), 7.09 (2H, d, J=8.5 Hz)

EXAMPLE 3

2-[2-Bromo-4-[2-[[(1S,2R)-2-hydroxy-2-(4-hydroxyphenyl)-1-ethylethyl]amino]ethyl phenoxy] acetic acid (Compound 24)

To a solution of ethyl 2-[2-bromo-4-[2-[[(1S,2R)-2-hydroxy-2-(4-hydroxyphenyl)-1-methylethyl]amino]ethyl]phenoxy]acetate (327 mg) in ethanol (3.3 ml) was added 1N aqueous sodium hydroxide solution (1.45 ml), and the mixture was stirred for 15 hours at room temperature. 1N Hydrochloric acid (1.45 ml) was added to the stirred reaction mixture under ice-cooling, and the solvent was removed under reduced pressure. To the residue was added water, and the resulting insoluble material was collected by filtration to give 2-[2-bromo-4-[2-[[(1S,2R)-2-hydroxy-2-(4-hydroxyphenyl)-1-methylethyl]amino]ethyl]phenoxy]acetic acid (88 mg).

¹H-NMR(DMSO-d₆) δ ppm: 0.90 (3H, d, J=6.6 Hz), 2.50–2.75 (2H, m), 2.90–3.40 (3H, m), 4.46 (2H, s), 5.00–5.10 (1H, m), 6.65–6.90 (4H, m), 7.14 (2H, d, J=8.5 Hz), 7.36 (1H, d, J=2.0 Hz), 9.35 (2H, br)

Specific Rotation: $[\alpha]_D^{32}$=−8.3° (c=0.63, Acetic acid)

EXAMPLE 4

The following compounds were prepared according to a similar manner to that described in Example 3 using the corresponding phenoxyacetate derivative.

2-[2-Chloro-4-[2-[[(1S,2R)-2-hydroxy-2-(4-hydroxyphenyl)-1-methylethyl]amino]ethyl]phenoxy]acetic acid (Compound 25)

¹H-NMR(DMSO-d₆+D₂O) δ ppm: 0.93 (3H, d, J=6.7 Hz), 2.68–2.82 (2H, m), 3.00–3.17 (2H, m), 3.26–3.35 (1H, m), 4.47 (2H, s), 5.06 (1H, d, J=2.2 Hz), 6.75 (2H, d, J=8.5 Hz), 6.83 (1H, d, J=8.6 Hz), 6.91 (1H, dd, J=8.6, 2.1 Hz), 7.17 (2H, d, J=8.5 Hz), 7.26 (1H, d, J=2.1 Hz)

Specific Rotation: $[\alpha]_D^{32}$=−5.7° (c=1.01, Acetic acid)

2-[2,6-Dichloro-4-[[2-[[(1S,2R)-2-hydroxy-2-(4-hydroxyphenyl)-1-methylethyl]amino]ethyl]phenoxy]acetic acid (Compound 26)

¹H-NMR(DMSO-d,) δ ppm: 0.88 (3H, d, J=6.6 Hz), 2.60–2.80 (2H, m), 2.95–3.20 (3H, m), 4.40–4.55 (2H, m), 4.85–5.00 (1H, m), 6.71 (2H, d, J=8.6 Hz), 7.13 (2H, d, J=8.6 Hz), 7.24 (2H, s), 9.40 (1H, br)

Specific Rotation: $[\alpha]_D^{30}$=−17.20° (c=0.50, Dimethyl sulfoxide)

2-[2,5-Dichloro-4-[2-[[(1S,2R)-2-hydroxy-2-(4-hydroxyphenyl)-1-methylethyl]amino]ethyl]phenoxy]acetic acid (Compound 27)

¹H-NMR(DMSO-d₆) δ ppm: 0.86 (3H, d, J=6.6 Hz), 2.30–2.70 (2H, m), 2.85–3.05 (2H, m), 3.15–3.35 (1H, m) 4.45–4.60 (2H, m) 5.17 (1H, br s), 6.72 (2H, d, J=8.6 Hz), 6.91 (1H, s), 7.16 (2H, d, J=8.6 Hz), 7.19 (1H, s), 9.33 (1H, br)

Specific Rotation: $[\alpha]_D^{31}$=−13.1° (c=1.00, 1N Hydrochloric acid)

2-[2-Fluoro-4-[2-[[(1S,2R)-2-hydroxy-2-(4-hydroxyphenyl)-1-methylethyl]amino]ethyl]phenoxy]acetic acid (Compound 28)

¹H-NMR(DMSO-d₆) δ ppm: 0.89 (3H, d, J=6.6 Hz), 2.40–2.70 (2H, m), 2.90–3.10 (2H, m), 3.15–3.30 (1H, m), 4.25–4.55 (3H, m), 5.11 (1H, br s), 6.55–6.65 (1H, m), 6.71 (2H, d, J=8.5 Hz), 6.81 (1H, t, J=8.8 Hz), 6.98 (1H, dd, J=12.6, 1.8 Hz), 7.14 (2H, d, J=8.5 Hz), 9.36 (2H, br)

Specific Rotation: $[\alpha]_D^{32}$=−8.2° (c=1.49, Acetic acid)

2-(4-[2-[[(1S,2R)-2-Hydroxy-2-(4-hydroxyphenyl)-1-methylethyl]amino]ethyl]-2-methoxyphenoxy]acetic acid (Compound 29)

¹H-NMR(DMSO-d₆) δ ppm: 0.91 (3H, d, J=6.4 Hz) 2.40–3.30 (5H, m), 3.74 (3H, s), 4.34 (2H, s), 5.07 (1H, br), 6.38 (1H, d, J=6.9 Hz), 6.60–6.80 (4H, m), 7.14 (2H, d, J=8.4 Hz), 9.40 (2H, br)

Specific Rotation: $[\alpha]_D^{32}$=−11.0° (c=0.51, Acetic acid)

2-[2-Ethoxy-4-[2-[[(1S,2R)-2-hydroxy-2-(4-hydroxyphenyl)-1-methylethyl]amino]ethyl]phenoxy]acetic acid (Compound 30)

¹H-NMR(DMSO-d₆) δ ppm: 0.90 (3H, d, J=6.5 Hz), 1.32 (3H, t, J=7.0 Hz), 2.50–3.15 (5H, m), 3.98 (2H, q, J=7.0 Hz), 4.26 (2H, s), 4.85 (1H, br), 6.38 (1H, d, J=8.3 Hz), 6.60 (1H, d, J=8.3 Hz), 6.65–6.75 (3H, m), 7.08 (2H, d, J=8.3 Hz), 9.60 (1H, br)

Specific Rotation: $[\alpha]_D^{32}$=−8.0° (c=0.20, Acetic acid)

2-[2-Benzyloxy-4-[2-[[(1S,2R)-2-hydroxy-2-(4-hydroxyphenyl)-1-methylethyl]amino]ethyl]phenoxy]acetic acid (Compound 31)

¹H-NMR(DMSO-d₆) δ ppm: 0.90 (3H, d, J=6.6 Hz) 2.55–2.75 (2H, m), 2.85–3.10 (2H, m), 3.15–3.30 (1H, m), 4.37 (2H, s), 5.00–5.15 (3H, m), 6.38 (1H, d, J=8.3 Hz), 6.65 (1H, d, J=8.3 Hz), 6.71 (2H, d, J=8.5 Hz), 6.82 (1H, s), 7.13 (2H, d, J=8.5 Hz), 7.30–7.55 (5H, m), 9.40 (2H, br)

Specific Rotation: $[\alpha]_D^{32}$=−3.5° (c=0.17, Acetic acid)

2-[5-Chloro-4-[2-[[(1S,2R)-2-hydroxy-2-(4-hydroxyphenyl)-1-methylethyl]amino]ethyl]-2-methoxyphenoxy]acetic acid (Compound 32)

¹H-NMR(DMSO-d₆) δ ppm: 0.90 (3H, d, J=6.5 Hz), 2.30–3.50 (5H, m), 3.77 (3H, s), 4.40–4.55 (2H, m), 5.10 (1H, br s), 6.73 (2H, d, J=8.5 Hz), 6.78 (2H, s), 7.16 (2H, d, J=8.5 Hz), 9.35 (2H, br)

Specific Rotation: $[\alpha]_D^{30}$=−16.8° (c=0.25, Dimethyl sulfoxide)

2-[4-[2-[[(1S,2R)-2-Hydroxy-2-(4-hydroxyphenyl)-1-methylethyl]ethyl]amino]ethyl]-2-methylphenoxy]acetic acid (Compound 33)

¹H-NMR(DMSO-d₆+D₂O) δ ppm: 0.96 (3H, d, J=6.7 Hz), 2.19 (3H, s), 2.87 (2H, t, J=8.3 Hz), 3.07–3.22 (2H, m), 3.30–3.39 (1H, m), 4.61 (2H, s), 4.99 (1H, br s), 6.70–6.82 (3H, m), 7.01 (1H, d, J=8.2 Hz), 7.06 (1H, s), 7.17 (2H, d, J=8.5 Hz)

Specific Rotation: $[\alpha]_D^{32}$=−4.6° (c=1.01, Acetic acid)

2-[2-Ethyl-4-[[(1S,2R)-2-hydroxy-2-(4-hydroxyphenyl)-1-methylethyl]amino]ethyl]phenoxy]acetic acid (Compound 34)

¹H-NMR(DMSO-d₆) δ ppm: 0.90 (3H, d, J=6.5 Hz), 1.14 (3H, t, J=7.5 Hz), 2.50–2.70 (4H, m), 2.80–3.00 (2H, m), 3.05–3.20 (1H, m) 4.34 (2H, s), 4.96 (1H, br s) 6.55–6.75 (4H, m), 6.85 (1H, s), 7.10 (2H, d, J=8.4 Hz), 9.50 (2H, br)

Specific Rotation: $[\alpha]_D^{25}$=−8.7° (c=1.04, Acetic acid)

2-[4-[2-[[(1S,2R)-2-Hydroxy-2-(4-hydroxyphenyl)-1-methylethyl]amino]ethyl]-2,5-dimethylphenoxy]acetic acid (Compound 35)

¹H-NMR(DMSO-d₆) δ ppm: 0.88 (3H, d, J=6.6 Hz), 1.82 (3H, s), 2.12 (3H, s), 2.30–2.50 (2H, m), 2.75–2.95 (2H, m), 3.20–3.40 (1H, m), 4.30–4.50 (2H, m), 5.13 (1H, br s), 6.46 (1H, s), 6.72 (2H, d, J=8.6 Hz), 6.74 (2H, s), 7.16 (2H, d, J=8.6 Hz)

Specific Rotation: $[\alpha]_D^{32}$=−30.5° (c=0.61, Dimethyl sulfoxide)

2-[4-[2-[[(1S,2R)-2-Hydroxy-2-(4-hydroxyphenyl)-1-methylethyl]amino]ethyl]-2-(trifluoromethyl)phenoxy]acetic acid hydrochloride (Compound 36)

¹H-NMR(DMSO-d₆+D₂O) δ ppm: 0.97 (3H, d, J=6.7 Hz), 2.90–3.45 (5H, m), 4.79 (2H, s), 4.99 (1H, d, J=2.4 Hz), 6.78 (2H, d, J=8.5 Hz), 7.08 (1H, d, J=8.6 Hz), 7.18 (2H, d, J=8.5 Hz), 7.45–7.55 (1H, m), 7.57 (1H, d, J=1.9 Hz)

Specific Rotation: $[\alpha]_D^{32}$=−5.7° (c=1.01, Acetic acid)

2-[2-Cyano-4-[2-[[(1S,2R)-2-hydroxy-2-(4-hydroxyphenyl)-1-methylethyl]amino]ethyl]phenoxy]acetic acid (Compound 37)

$^1$H-NMR(DMSO-d$_6$+D$_2$O) δ ppm: 0.97 (3H, d, J=6.4 Hz), 2.60–2.80 (2H, m), 3.00–3.35 (3H, m), 4.49 (2H, s), 5.05 (1H, br s), 6.74 (2H, d, J=8.3 Hz), 6.89 (1H, d, J=8.7 Hz), 7.16 (2H, d, J=8.3 Hz), 7.21 (1H, d, J=8.7 Hz), 7.51 (1H, s)

Specific Rotation: $[\alpha]_D^{32}$=−5.7° (c=1.05, Acetic acid)

2-[4-[2-[[(1S,2R)-2-Hydroxy-2-(4-hydroxyphenyl)-1-methylethyl]amino]ethyl]-2-nitrophenoxy]acetic acid (Compound 38)

$^1$H-NMR(DMSO-d$_6$) δ ppm: 0.95 (3H, d, J=6.7 Hz) 2.90–3.05 (2H, m), 3.15–3.40 (3H, m), 4.85 (2H, s), 5.05–5.15 (1H, m), 6.05 (1H, br), 6.76 (2H, d, J=8.5 Hz), 7.16 (2H, d, J=8.5 Hz), 7.22 (1H, d, J=8.7 Hz), 7.50 (1H, dd, J=8.7, 2.1 Hz), 7.81 (1H, d, J=2.1 Hz), 8.90 (1H, br), 9.40 (1H, br)

Specific Rotation: $[\alpha]_D^{25}$=−4.4° (c=0.63, 1N Hydrochloric acid)

2-[2-Carbamoyl-4-[2-[[(1S,2R)-2-hydroxy-2-(4-hydroxyphenyl)-1-methylethyl]amino]ethyl]phenoxy]acetic acid (Compound 39)

$^1$H-NMR(DMSO-d$_6$) δ ppm: 0.87 (3H, d, J=6.4 Hz), 2.60–2.90 (5H, m), 4.33 (2H, s), 4.47 (1H, br s), 5.10 (1H, br), 6.65 (2H, d, J=8.5 Hz), 6.92 (1H, d, J=8.5 Hz), 7.01 (2H, d, J=8.5 Hz), 7.05–7.20 (2H, m), 7.22 (1H, br s), 7.56 (1H, d, J=2.0 Hz), 9.54 (1H, br s)

Ethyl 2-[2-Formylamino-4-[2-[[(1S,2R)-2-hydroxy-2-(4-hydroxyphenyl)-1-methylethyl]amino]ethyl]phenoxy]acetate (Compound 40)

$^1$H-NMR(DMSO-d$_6$) δ ppm: 0.80–1.00 (3H, m), 2.50–4.00 (5H, m), 4.20–5.40 (3H, m), 6.60–8.70 (8H, m)

Specific Rotation: $[\alpha]_D^{25}$=−9.6° (c=0.25, Acetic acid)

2-[2-Chloro-4-[2-[[(1S,2R)-2-hydroxy-2-(4-hydroxyphenyl)-1-methylethyl]amino]ethyl]-5-methoxyphenoxy]acetic acid (Compound 41)

$^1$H-NMR(DMSO-d$_6$) δ ppm: 0.88 (3H, d, J=6.6z), 2.30–2.60 (2H, m), 2.80–2.95 (2H, m), 3.15–3.30 (1H, m), 3.67 (3H, s), 4.45–4.60 (2H, m) 5.09 (1H, br s), 6.53 (1H, s), 6.72 (2H, d, J=8.5 Hz), 6.98 (1H, s), 7.15 (2H, d, J=8.5 Hz)

Specific Rotation: $[\alpha]_D^{31}$=−6.8° (c=1.00, Acetic acid)

2-[5-Chloro-2-ethoxy-4-[2-[[(1S,2R)-2-hydroxy-2-(4-hydroxyphenyl)-1-methylethyl]amino]ethyl]phenoxy]acetic acid (Compound 42)

$^1$H-NMR(DMSO-d$_6$) δ ppm: 0.87 (3H, d, J=6.6 Hz), 1.34 (3H, t, J=7.0 Hz), 2.30–2.65 (2H, m), 2.80–2.95 (2H, m), 3.15–3.30 (1H, m), 3.98 (2H, q, J=7.0 Hz), 4.30–4.50 (2H, m), 5.13 (1H, br s), 6.67 (1H, s), 6.68 (1H, s), 6.72 (2H, d, J=8.5 Hz), 7.15 (2H, d, J=8.5 Hz), 9.37 (1H, br)

Specific Rotation: $[\alpha]_D^{30}$=−7.2° (c=1.10, 1N Hydrochloric acid)

2-[2-(Dimethylaminocarbonyl)-4-[2-[[(1S,2R)-2-hydroxy-2-(4-hydroxyphenyl)-1-methylethyl]amino]ethyl]phenoxy]acetic acid (Compound 43)

$^1$H-NMR(DMSO-d$_6$) δ ppm: 0.96 (3H, d, J=6.7 Hz), 2.81 (3H, s), 2.90–3.05 (5H, m), 3.15–3.65 (3H, m), 4.70–4.90 (2H, m), 5.05 (1H, br s), 5.90 (1H, br), 6.76 (2H, d, J=8.5 Hz), 6.85–6.95 (1H, m), 7.10–7.30 (4H, m), 8.72 (2H, br), 9.36 (1H, br), 13.00 (1H, br)

Specific Rotation: $[\alpha]_D^{25}$=−2.7G (c=0.37, Acetic acid)

2-[2-Chloro-4-[2-[(1S,2R)-2-hydroxy-2-(4-hydroxyphenyl)-1-methylethyl]amino]ethyl]-5-methylphenoxy]acetic acid (Compound 44)

$^1$H-NMR(DMSO-d$_6$) δ ppm: 0.88 (3H, d, J=6.63 Hz), 1.78 (3H, s), 2.25–2.35 (1H, m), 2.40–2.50 (1H, m), 2.85–3.00 (2H, m), 3.20–3.50 (1H, m), 4.40–4.50 (2H, m), 5.20 (1H, m), 6.62 (1H, s), 6.72 (2H, d, J=8.47 Hz) 7.02 (1H, s), 7.17 (2H, d, J=8.47 Hz), 9.33 (1H, br s)

2-[2,5-Difluoro-4-[2-[(1S,2R)-2-hydroxy-2-(4-hydroxyphenyl)-1-methylethyl]amino]ethyl]phenoxy]acetic acid (Compound 45)

$^1$-NMR(DMSO-d$_6$) δ ppm: 0.87 (3H, d, J=6.6 Hz), 2.25–2.60 (2H, m), 2.90–3.00 (2H, m), 3.15–3.30 (1H, m), 4.45–4.60 (2H, m), 5.12 (1H, br s), 6.72 (2H, d, J=8.5 Hz), 6.77 (1H, dd, J=11.4, 7.3 Hz), 6.97 (1H, dd, J=11.8, 7.2 Hz), 7.14 (2H, d, J=8.5 Hz), 9.30 (1H, br)

EXAMPLE 5

2-[2-Hydroxy-4-[2-[[(1S,2R)-2-hydroxy-2-(4-hydroxyphenyl)-1-methylethyl]amino]ethyl]phenoxy]acetic acid (Compound 46)

To a solution of 2-[2-benzyloxy-4-[2-[[(1S,2R)-2-hydroxy-2-(4-hydroxyphenyl)-1-methylethyl]amino]ethyl]phenoxy]acetic acid (97 mg) in acetic acid (4 ml) was added 10% palladium carbon (wet, 50% water) (30 mg), and the mixture was stirred for 50 minutes at room temperature under a hydrogen atmosphere. The catalyst was filtered off, and the solvent was removed under reduced pressure. After addition of ethyl acetate to the residue, collection of the resulting insoluble material by filtration gave 2-[2-hydroxy-4-[2-[[(1S,2R)-2-hydroxy-2-(4-hydroxyphenyl)-1-methylethyl]amino]ethyl]phenoxy]acetic acid (77 mg).

$^1$H-NMR(DMSO-d$_6$) δ ppm: 0.93 (3H, d, J=6.6 Hz), 2.75–2.90 (2H, m), 3.05–3.50 (3H, m), 4.12 (2H, s), 5.00 (1H, br s), 6.05 (1H, br), 6.51 (1H, dd, J=8.0, 1.6 Hz), 6.65 (1H, d, J=1.6 Hz), 6.74 (2H, d, J=8.5 Hz), 6.83 (1H, d, J=8.0 Hz), 7.15 (2H, d, J=8.5 Hz), 8.90 (1H, br), 9.45 (1H, br)

Specific Rotation: $[\alpha]_D^{25}$=−3.7° (c=0.27, Acetic acid)

EXAMPLE 6

2-[2-Dimethylamino-4-[2-[[(1S,2R)-2-hydroxy-2-(4-hydroxyphenyl)-1-methylethyl]amino]ethyl]phenoxy]acetic acid (Compound 47)

N,N-Dimethyl-2-[2-dimethylamino-4-[2-[[(1S,2R)-2-hydroxy-2-(4-hydroxyphenyl)-1-methylethyl]amino]ethyl]phenoxy]acetamide (503 mg) was dissolved in 1N aqueous sodium hydroxide solution (6.0 ml), and the solution was stirred for 20 hours at room temperature. 1N Hydrochloric acid (6.0 ml) was added to the stirred reaction mixture under ice-cooling, and direct purification of the resulting mixture by medium pressure liquid column chromatography on ion exchange resin (Nippon Rensui Co. Ltd., DIAION® HP-20) (eluent:water/methanol=1/0 to 1/1) gave 2-[2-dimethylamino-4-[2-[[(1S,2R)-2-hydroxy-2-(4-hydroxyphenyl)-1-methylethyl]amino]ethyl]phenoxy]acetic acid (330 mg).

$^1$H-NMR(DMSO-d$_6$) δ ppm: 0.89 (3H, d, J=6.6 Hz), 2.50–2.75 (8H, m), 2.85–3.05 (2H, m), 3.15–3.25 (1H, m), 4.37 (2H, s), 5.05 (1H, br s), 6.40 (1H, dd, J=8.3, 1.7 Hz), 6.55–6.65 (2H, m), 6.70 (2H, d, J=8.6 Hz), 7.13 (2H, d, J=8.6 Hz)

Specific Rotation: $[\alpha]_D^{32}=-0.9°$ (c=1.06, Acetic acid)

EXAMPLE 7

Ethyl 2-[2-chloro-4-[2-[[(1S,2R)-2-hydroxy-2-(4-hydroxyphenyl)-1-methylethyl]amino]ethyl]phenoxy]acetate hydrochloride (Compound 48)

To a stirred solution of ethyl 2-[2-chloro-4-[2-[[(1S,2R)-2-hydroxy-2-(4-hydroxyphenyl)-1-methylethyl]amino]ethyl]phenoxy]acetate (390 mg) in ethyl acetate (5 ml) was added 4N hydrogen chloride solution in ethyl acetate (500 μl) at room temperature, and the mixture was stirred for 15 minutes. After removal of the solvent under reduced pressure, diethyl ether was added to the residue. Collection of the resulting insoluble material by filtration gave ethyl 2-[2-chloro-4-[2-[[(1S,2R)-2-hydroxy-2-(4-hydroxyphenyl)-1-methylethyl]amino]ethyl]phenoxy]acetate hydrochloride (400 mg).

$^1$H-NMR(DMSO-$d_6$) δ ppm: 0.96 (3H, d, J=6.7 Hz), 1.21 (3H, t, J=7.1 Hz), 2.90–3.05 (2H, m), 3.15–3.40 (3H, m), 4.17 (2H, q, J=7.1 Hz), 4.90 (2H, s), 5.08 (1H, br s), 5.90–6.00 (1H, m), 6.76 (2H, d, J=8.6 Hz), 7.02 (1H, d, J=8.6 Hz), 7.10–7.20 (3H, m), 7.40 (1H, d, J=2.1 Hz), 8.85 (2H, br), 9.41 (1H, s)

Specific Rotation: $[\alpha]_D^{30}=-10.3°$ (c=1.00, Ethanol)

EXAMPLE 8

Ethyl 2-[2,5-dichloro-4-[2-[[(1S,2R)-2-hydroxy-2-(4-hydroxyphenyl)-1-methylethyl]amino]ethyl]phenoxy]acetate hydrochloride (Compound 49)

Ethyl 2-[2,5-dichloro-4-[2-[[(1S,2R)-2-hydroxy-2-(4-hydroxyphenyl)-1-methylethyl]amino]ethyl]phenoxy]acetate hydrochloride was prepared according to a similar manner to that described in Example 7 using the corresponding phenoxyacetate derivative.

$^1$H-NMR(DMSO-$d_6$) δ ppm: 0.97 (3H, d, J=6.7 Hz), 1.22 (3H, t, J=7.1 Hz), 3.00–3.45 (5H, m) 4.18 (2H, q, J=7.1 Hz), 4.98 (2H, s), 5.07 (1H, brs), 5.97 (1H, d, J=4.2 Hz), 6.76 (2H, d, J=8.5 Hz), 7.18 (2H, d, J=8.5 Hz), 7.27 (1H, s), 7.55 (1H, s), 8.85 (2H, br), 9.41 (1H, s)

Specific Rotation: $[\alpha]_D^{30}=-7.1°$ (c=1.04, Ethanol)

EXAMPLE 9

Ethyl 2-[2-chloro-4-[2-[[(1S,2R)-2-hydroxy-2-(4-hydroxyphenyl)-1-methylethyl]amino]ethyl]phenoxy]acetate methanesulfonate (Compound 50)

To a stirred solution of ethyl 2-[2-chloro-4-[2-[[(1S,2R)-2-hydroxy-2-(4-hydroxyphenyl)-1-methylethyl]amino]ethyl]phenoxy]acetate (770 mg) in ethanol (4 ml) was added methanesulfonic acid (79 μl) at room temperature, and the mixture was stirred for 30 minutes. Collection of the resulting precipitates by filtration gave ethyl 2-[2-chloro-4-[2-[[(1S,2R)-2-hydroxy-2-(4-hydroxyphenyl)-1-methylethyl]amino]ethyl]phenoxy]acetate methanesulfonate (220 mg).

$^1$H-NMR(DMSO-$d_6$) δ ppm: 0.95 (3H, d, J=6.6 Hz), 1.22 (3H, t, J=7.1 Hz), 2.32 (3H, s), 2.85–3.00 (2H, m), 3.10–3.42 (3H, m), 4.17 (2H, q, J=7.1 Hz), 4.90 (2H, s), 5.00 (1H, m), 5.95 (1H, m), 6.76 (2H, d, J=8.5 Hz), 7.02 (1H, d, J=8.5 Hz), 7.17 (2H, d, J=8.5 Hz), 7.18 (1H, d, J=8.5 Hz), 7.40 (1H, s), 8.39–8.65 (2H, m), 9.39 (1H, s)

Specific Rotation: $[\alpha]_D^{25}=-8.8)$ (c=1.05, Methanol)

Test Example 1

The Experiment for Measuring $\beta_3$-adrenoceptor Stimulating Effects

Urinary bladders of male ferrets (1100 to 1400 g in body weight) were isolated and urinary bladder smooth muscle strips of approximately 10 mm in length and approximately 2 mm in width were prepared. The experiment was conducted according to the Magnus method. The preparations with a tension of 1 g were exposed to Krebs-Henseleit solution maintained at 37° C. and gassed with a mixture of 95% oxygen and 5% carbon dioxide. Basal tensions of urinary bladder were isometrically measured with a force-displacement transducer and recorded. A test compound was cumulatively added to the Magnus bath every about 5 minutes. Tension of urinary bladder smooth muscle before addition of the test compound was expressed as 100% and tension of maximal relaxation induced by $10^{-5}$M of forskolin was expressed as 0%. The drug efficacy was evaluated as the concentration of the test compound required to produce 50% of the relaxation (i.e., $EC_{50}$ was shown in the following Table 1.

TABLE 1

| Compound No. | $EC_{50}$ value (M) |
| --- | --- |
| 24 | $3.1 \times 10^{-9}$ |
| 25 | $4.2 \times 10^{-9}$ |
| 26 | $1.7 \times 10^{-8}$ |
| 27 | $1.9 \times 10^{-9}$ |
| 28 | $1.9 \times 10^{-8}$ |
| 29 | $9.8 \times 10^{-9}$ |
| 30 | $6.8 \times 10^{-8}$ |
| 31 | $1.1 \times 10^{-8}$ |
| 33 | $1.6 \times 10^{-8}$ |
| 35 | $1.0 \times 10^{-8}$ |
| 36 | $1.3 \times 10^{-7}$ |
| 37 | $5.3 \times 10^{-9}$ |
| 38 | $1.6 \times 10^{-8}$ |
| 40 | $4.1 \times 10^{-8}$ |
| 43 | $3.4 \times 10^{-7}$ |
| 46 | $6.5 \times 10^{-9}$ |
| 47 | $6.3 \times 10^{-8}$ |
| 48 | $7.4 \times 10^{-9}$ |
| 49 | $7.2 \times 10^{-10}$ |
| (R,R)-BRL-37344 | $1.6 \times 10^{-9}$ |

Test Example 2

The Experiment for Measuring $\beta_1$-adrenoceptor Stimulating Effects

Atria of male SD rats (250 to 400 g in body weight) were isolated and the experiment was conducted according to the Magnus method. The preparations with a tension of 0.5 g were exposed to Krebs-Henseleit solution maintained at 37° C. and gassed with a mixture of 95% oxygen and 5% carbon dioxide. The cardiac contractility was isometrically measured with a force-displacement transducer, and heart rate was recorded via a tachometer. A test compound was added cumulatively. Increase of heart rate per minute after addition of $10^{-8}$M isoproterenol was expressed as 100%. The drug efficacy was evaluated as the concentration of the test compound required to produce 50% increase of heart rate per minute (i.e., $EC_{50}$ value). The result was shown in the following Table 2.

TABLE 2

| Compound No. | $EC_{50}$ value (M) |
|---|---|
| 24 | $>10^{-4}$ |
| 25 | $7.0 \times 10^{-5}$ |
| 26 | $>10^{-4}$ |
| 27 | $4.9 \times 10^{-5}$ |
| 28 | $3.0 \times 10^{-5}$ |
| 29 | $>10^{-4}$ |
| 30 | $>10^{-4}$ |
| 31 | $>10^{-4}$ |
| 33 | $3.1 \times 10^{-5}$ |
| 35 | $3.8 \times 10^{-5}$ |
| 36 | $>10^{-4}$ |
| 37 | $3.3 \times 10^{-5}$ |
| 38 | $5.8 \times 10^{-5}$ |
| 40 | $3.5 \times 10^{-6}$ |
| 43 | $5.8 \times 10^{-5}$ |
| 46 | $2.1 \times 10^{-5}$ |
| 47 | $>10^{-4}$ |
| 48 | $1.7 \times 10^{-5}$ |
| 49 | $6.8 \times 10^{-6}$ |
| (R,R)-BRL-37344 | $2.7 \times 10^{-7}$ |

Test Example 3

The Experiment for Measuring $\beta_2$-adrenoceptor Stimulating Effects

Uteri of pregnant SD rats (pregnancy day 21) were isolated and longitudinal strips of approximately 15 mm in length and approximately 5 mm in width free from the basal plate were prepared. The experiment was conducted according to the Magnus method. The preparations with a tension of 0.5 g were exposed to Locke-Ringer solution maintained at 37° C. and gassed with a mixture of 95% oxygen and 5% carbon dioxide. Spontaneous contractions of myometrium were isometrically measured with a force-displacement transducer and recorded. A test compound was cumulatively added to the Magnus bath every 5 minutes. The drug efficacy was evaluated as the concentration of the test compound required to produce 50% of the inhibition of uterine contraction (i.e., $EC_{50}$ value) by comparing the sum of uterine contraction during 5 minutes after addition of the test compound with the sum of uterine contractions during 5 minutes before addition of the test compound which was expressed as 100%. The result was shown in the following Table 3.

TABLE 3

| Compound No. | $EC_{50}$ value (M) |
|---|---|
| 24 | $1.0 \times 10^{-5}$ |
| 25 | $1.4 \times 10^{-5}$ |
| 26 | $1.4 \times 10^{-6}$ |
| 27 | $4.9 \times 10^{-7}$ |
| 28 | $1.8 \times 10^{-6}$ |
| 29 | $3.9 \times 10^{-6}$ |
| 30 | $2.5 \times 10^{-5}$ |
| 31 | $1.9 \times 10^{-6}$ |
| 33 | $1.3 \times 10^{-5}$ |
| 35 | $1.8 \times 10^{-6}$ |
| 36 | $2.0 \times 10^{-5}$ |
| 37 | $7.6 \times 10^{-5}$ |
| 38 | $2.6 \times 10^{-6}$ |
| 40 | $1.0 \times 10^{-6}$ |
| 43 | $5.3 \times 10^{-5}$ |
| 46 | $2.1 \times 10^{-7}$ |
| 47 | $1.7 \times 10^{-5}$ |
| 48 | $5.2 \times 10^{-7}$ |

TABLE 3-continued

| Compound No. | $EC_{50}$ value (M) |
|---|---|
| 49 | $6.1 \times 10^{-8}$ |
| (R,R)-BRL-37344 | $9.0 \times 10^{-9}$ |

Test Example 4

Acute Toxicity

To male ICR rats of 4 weeks age was administered orally ethyl 2-[2-chloro-4-[2-[[(1S,2R)-2-hydroxy-2-(4-hydroxyphenyl)1-methylethyl]amino]ethyl]phenoxy]acetate hydrochloride at a does of 2 g/kg. No death of animals was observed during 24 hours after the administration with the time course.

What is claimed is:

1. A phenoxyacetic acid derivative represented by the general formula:

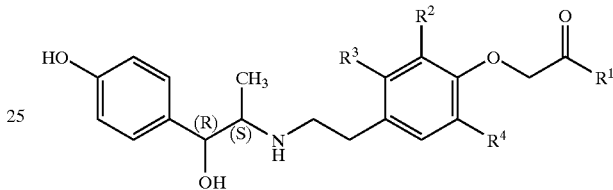

wherein $R^1$ represents a hydroxy group, a lower alkoxy group, an aralkoxy group, an amino group, or a mono or di(lower alkyl)amino group; one of $R^2$ and $R^3$ is a hydrogen atom, a halogen atom, a lower alkyl group or a lower alkoxy group, while the other is a hydrogen atom; $R^4$ represents a halogen atom, a lower alkyl group, a halo(lower alkyl) group, a hydroxy group, a lower alkoxy group, an aralkoxy group, a cyano group, a nitro group, an amino group, a mono or di(lower alkyl)amino group, a carbamoyl group, a mono or di(lower alkyl)carbamoyl group or a group represented by the general formula:

—$NHCOR^5$ (wherein $R^5$ represents a hydrogen atom or a lower alkyl group); the carbon atom marked with (R) represents a carbon atom in R configuration; and the carbon atom marked with (S) represents a carbon atom in S configuration, or a pharmaceutically acceptable salt thereof.

2. A phenoxyacetic acid derivative represented by the general formula:

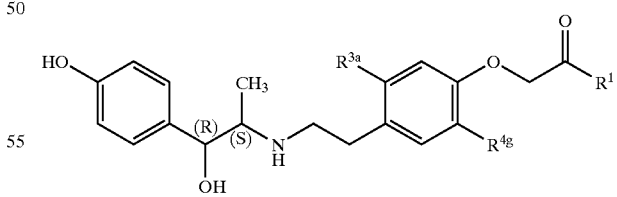

wherein $R^{1b}$ represents a hydroxy group or a lower alkoxy group; $R^{3a}$ is a hydrogen atom, a lower alkyl group or a halogen atom; $R^{4g}$ represents a lower alkyl group, a halogen atom or a hydroxy group; the carbon atom marked with (R) represents a carbon atom in R configuration; and the carbon atom marked with (S) represents a carbon atom in S configuration, or a pharmaceutically acceptable salt thereof.

3. A phenoxyacetic acid derivative as claimed in claim 2, selected from the group consisting of 2-[2-bromo-4-[2-

[[(1S,2R)-2-hydroxy-2-(4-hydroxyphenyl)-1-methylethyl] amino]ethyl]phenoxy]acetic acid, 2-[2-chloro-4-[2-[[(1S,2R)-2-hydroxy-2-(4-hydroxyphenyl)-1-methylethyl]amino]ethyl]phenoxy]acetic acid, 2-[2,5-dichloro-4-[2-[[(1S,2R)-2-hydroxy-2-(4-hydroxyphenyl)-1-methylethyl]amino]ethyl]phenoxy]acetic acid, 2-[4-[2-[[(1S,2R)-2-hydroxy-2-(4-hydroxyphenyl)-1-methyl-ethyl]amino]ethyl]-2,5-dimethylphenoxy]acetic acid, 2-[2-hydroxy-4-[2-[[(1S,2R)-2-hydroxy-2-(4-hydroxyphenyl)-1-methylethyl]amino]ethyl]phenoxy]acetic acid, ethyl 2-[2-chloro-4-[2-[[(1S,2R)-2-hydroxy-2-(4-hydroxyphenyl)-1-methylethyl]amino]ethyl]phenoxy]acetate, ethyl 2-[2,5-dichloro-4-[2-[[(1S,2R)-2-hydroxy-2-(4-hydroxyphenyl)-1-methylethyl]amino]ethyl]phenoxy]acetate, ethyl 2-[4-[2-[[(1S, 2R)-2-hydroxy-2-(4-hydroxyphenyl)-1-methylethyl]amino]ethyl]-2,5-dimethylphenoxy]acetate, and a pharmaceutically acceptable salt thereof.

4. A pharmaceutical composition comprising as the active ingredient a phenoxyacetic acid derivative as claimed in claim 1, or a pharmaceutically acceptable salt thereof.

5. An agent for the prevention or treatment of obesity, hyperglycemia, the diseases caused by intestinal hypermotility, pollakiuria, urinary incontinence, depression, or the diseases caused by biliary calculi or hypermotility of biliary tract, which comprises as the active ingredient a phenoxyacetic acid derivative as claimed in claim 1, or a pharmaceutically acceptable salt thereof.

6. A method for the prevention or treatment of obesity, hyperglycemia, the diseases caused by intestinal hypermotility, pollakiuria, urinary incontinence, depression, or the diseases caused by biliary calculi or hypermotility of biliary tract, which comprises administering a therapeutically effective amount of a phenoxyacetic acid derivative as claimed in claim 1, or a pharmaceutically acceptable salt thereof.

7. A pharmaceutical composition comprising as the active ingredient a phenoxyacetic acid derivative as claimed in claim 2, or a pharmaceutically acceptable salt thereof.

8. An agent for the prevention or treatment of obesity, hyperglycemia, the diseases caused by intestinal hypermotility, pollakiuria, urinary incontinence, depression, or the diseases caused by biliary calculi or hypermotility of biliary tract, which comprises as the active ingredient a phenoxyacetic acid derivative as claimed in claim 2, or a pharmaceutically acceptable salt thereof.

9. A method for the prevention or treatment of obesity, hyperglycemia, the diseases caused by intestinal hypermotility, pollakiuria, urinary incontinence, depression, or the diseases caused by biliary calculi or hypermotility of biliary tract, which comprises administering a therapeutically effective amount of a phenoxyacetic acid derivative as claimed in claim 2, or a pharmaceutically acceptable salt thereof.

10. A pharmaceutical composition comprising as the active ingredient a phenoxyacetic acid derivative as claimed in claim 3, or a pharmaceutically acceptable salt thereof.

11. An agent for the prevention or treatment of obesity, hyperglycemia, the diseases caused by intestinal hypermotility, pollakiuria, urinary incontinence, depression, or the diseases caused by biliary calculi or hypermotility of biliary tract, which comprises as the active ingredient a phenoxyacetic acid derivative as claimed in claim 3, or a pharmaceutically acceptable salt thereof.

12. A method for the prevention or treatment of obesity, hyperglycemia, the diseases caused by intestinal hypermotility, pollakiuria, urinary incontinence, depression, or the diseases caused by biliary calculi or hypermotility of biliary tract, which comprises administering a therapeutically effective amount of a phenoxyacetic acid derivative as claimed in claim 3, or a pharmaceutically acceptable salt thereof.

* * * * *